US009267129B2

(12) United States Patent
Grundman et al.

(10) Patent No.: US 9,267,129 B2
(45) Date of Patent: Feb. 23, 2016

(54) COMPOSITIONS AND METHODS FOR CONFERRING HERBICIDE RESISTANCE

(71) Applicant: BEN-GURION UNIVERSITY OF THE NEGEV RESEARCH AND DEVELOPMENT AUTHORITY, Beer Sheva (IL)

(72) Inventors: Omer Grundman, Sde Boker (IL); Inna Khozin-Goldberg, Sde Boker (IL); Zvi Hacohen, Omer (IL); Michal Shapira, Rehovot (IL); Dina Raveh, Negev (IL); Sammy Boussiba, Omer (IL); Boris Zorin, Sde Boker (IL)

(73) Assignee: Ben-Gurion University of the Negev Research and Development Authority, Beer Sheva (IL)

( * ) Notice: Subject to any disclaimer, the term of this patent is extended or adjusted under 35 U.S.C. 154(b) by 0 days.

(21) Appl. No.: 14/349,359

(22) PCT Filed: Oct. 4, 2012

(86) PCT No.: PCT/IB2012/055347
§ 371 (c)(1),
(2) Date: Apr. 3, 2014

(87) PCT Pub. No.: WO2013/050966
PCT Pub. Date: Apr. 11, 2013

(65) Prior Publication Data

US 2014/0234976 A1 Aug. 21, 2014

Related U.S. Application Data

(60) Provisional application No. 61/543,339, filed on Oct. 5, 2011.

(51) Int. Cl.
*C12N 9/00* (2006.01)
*C12N 15/82* (2006.01)
(Continued)

(52) U.S. Cl.
CPC ................ *C12N 9/93* (2013.01); *C12N 9/0071* (2013.01); *C12N 9/1022* (2013.01); *C12N 15/52* (2013.01); *C12N 15/8251* (2013.01); *C12N 15/8274* (2013.01); *C12P 7/6427* (2013.01); *C12P 7/6463* (2013.01); *C12P 7/6472* (2013.01); *C12Y 202/01006* (2013.01)

(58) Field of Classification Search
CPC .................................................... C12N 9/0071
See application file for complete search history.

(56) References Cited

U.S. PATENT DOCUMENTS 6,884,602 B2 * 4/2005 Mueller et al. ............... 435/69.1

OTHER PUBLICATIONS

Muhitch., Acetolactate Synthase Activity in Developing Maize (*Zea mays* L.) Kernels, Plant Physiol. (1988), vol. 86, pp. 23-27.*

(Continued)

*Primary Examiner* — Alexander Kim
(74) *Attorney, Agent, or Firm* — Roach Brown McCarthy & Gruber, P.C.; Kevin D. McCarthy

(57) ABSTRACT

The present invention provides a protein, specifically Parietochloris incisa acetohydroxyacid synthase, and methods for producing branched-chain amino acid in a cell. The present invention further provides polypeptides and polynucleotides useful for conferring herbicide resistance in a cell or an organism. In particular, the present invention discloses a mutated acetohydroxyacid synthase which is resistant to herbicides.

9 Claims, 7 Drawing Sheets

| | | Position/ SEQ ID NO: | | Position/ SEQ ID NO: | | Position/ SEQ ID NO: | | |
|---|---|---|---|---|---|---|---|---|
| *C. reinhardtii* | IGTDAFQETP | 211/29 | MLGMHGTV | 356/30 | RAHTYLG | 595/31 | VLPMIP | 659/32 |
| *V. carteri* | IGTDAFQETP | 210/29 | MLGMHGTV | 355/30 | RAHTYLG | 593/31 | VLPMIP | 684/32 |
| *C. variabilis* | IGSDAFQETP | 158/29 | MLGMHGTV | 303/30 | RAHTYLG | 542/31 | VLPMIP | 635/32 |
| *B. napus* | IGTDAFQETP | 192/29 | MLGMHGTV | 337/30 | RAHTYLG | 571/31 | VLPMIP | 655/32 |
| *P. patens subsp* | IGTDAFQETP | 123/29 | MLGMHGTV | 268/30 | RAHTYLG | 502/31 | VLPMIP | 586/32 |
| | **:******* | | ******** | | ******* | | ****** | |

(51) Int. Cl.

| | |
|---|---|
| ***C12N 9/10*** | (2006.01) |
| ***C12N 15/52*** | (2006.01) |
| ***C12P 7/64*** | (2006.01) |
| ***C12N 9/02*** | (2006.01) |

(56) References Cited

OTHER PUBLICATIONS

CAA45116 last viewed on Jan. 30, 2015.*
Guo et al., Protein tolerance to random amino acid change, 2004, Proc. Natl. Acad. Sci. USA 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*
Wacey et al., Disentangling the perturbational effects of amino acid substitutions in the DNA-binding domain of p53., Hum Genet, 1999, vol. 104, pp. 15-22.*
Branden and Tooze, Introduction to Protein Structure (1999), 2nd edition, Garland Science Publisher, pp. 3-12.*
Bigogno C et al. Biosynthesis of arachidonic acid in the oleaginous micro alga Parietochloris incisa (Chlorophyceae): radiolabeling studies. Lipids 2002, 37, 209-216).
Ibdah M, et al. Homology modeling of the structure of bacterial acetohydroxy acid synthase and examination of the active site by site-directed mutagenesis. Biochemistry (N.Y.) 1996, 35, 16282-16291).
Grundman O et al. Cloning, mutagenesis, and characterization of the microalga Parietochloris incisa acetohydroxyacid synthase, and its possible use as an endogenous selection marker. Biotechnol Bioeng. Sep. 2012;109(9):2340-8. doi: 10.1002/bit.24515. Epub Apr. 17, 2012.
Chiara Bigogno et al., Lipid and fatty acid composition of the green oleaginous alga, Parietochloris incisa, the richest plant source of arachidonic acid, Phytochemistry 60 (2002) 497 503 vol. 60, No. 5, Jul. 1, 2002, pp. 497-503.
R.P. Funke et al., Nucleus-encoded plastid-target acetolactate synthase genes in two closely related chlorophytes, *Chlamydomonas reinhardtii* and *Volvox carteri*: phylogenetic origins and recent insertion of introns, Molecular and General Genetics MGG, vol. 262, No. 1, Aug. 25, 1999, pp. 12-21.
Joy L. Kovar et al., Molecular analysis of the acetolactate synthase gene of *Chlamydomonas reinhardtii* and development of a genetically engineered gene as a dominant selectable marker for genetic transformation, The Plant Journal, vol. 29, No. 1, Jan. 1, 2002, pp. 109-117.
Tara L Walker et al. Microalgae as bioreactors, Plant Cell Report, Springer, Berlin, DE, vol. 24, No. 11, Dec. 2005, pp. 629-641.

* cited by examiner

| | | Position/ SEQ ID NO: | | Position/ SEQ ID NO: | | Position/ SEQ ID NO: | | |
|---|---|---|---|---|---|---|---|---|
| *C. reinhardtii* | IGTDAFQETP | 211/29 | MLGMHGTV | 356/30 | RAHTYLG | 595/31 | VLPMIP | 659/32 |
| *V. carteri* | IGTDAFQETP | 210/29 | MLGMHGTV | 355/30 | RAHTYLG | 593/31 | VLPMIP | 684/32 |
| *C. variabilis* | IGSDAFQETP | 158/29 | MLGMHGTV | 303/30 | RAHTYLG | 542/31 | VLPMIP | 635/32 |
| *B. napus* | IGTDAFQETP | 192/29 | MLGMHGTV | 337/30 | RAHTYLG | 571/31 | VLPMIP | 655/32 |
| *P. patens subsp* | IGTDAFQETP | 123/29 | MLGMHGTV | 268/30 | RAHTYLG | 502/31 | VLPMIP | 586/32 |
| | **:******* | | ******** | | ******* | | ****** | |

Figure 1

```
SEQ ID NO:/organism
33/C. reinhardtii   -MKALRSGTAVARGQASCVSP----APRRPVSMSSQAMIPSISSPAAAAAPARSGRRALAVS 55
34/V. carteri       --MALRTCPTAAP-PRGCGTP----IQHPVTLLPHKALLPYSTAASRQAARPARVCVTAY 53
35/C. variabilis    -----------------------------------------------------------M 1
1/P.  incisa        MQGIMRPTAGALQQTVGCWHVPAGIPHAQQALRGRILPEELRQRCSATRPRAAARQSAVTA 60

33/C. reinhardtii   AKLADG-SRRMQS--------------------EEVRRAKEVAQAALAKDSPADWVDRYGSE 96
34/V. carteri       AKLADGSARRMQS--------------------EEVKRAKEVAQAALAKESPADWVDRFGSE 95
35/C. variabilis    AKDESKKANKASK---------------------AELEAARQAAQASLASEPPVEWVDRFNGQ 43
1/P.  incisa        AKLAEGKASTPSRSLRQQPAAPQQQQQQDSNELVALREAAKASLSSPAPAEWVDRFGSE 120
                    **   .. :    .                 *:   ::.*:*:*:. .*.:****:..:
33/C. reinhardtii   PRKGADILVQALEREGVDSVFAYPGGASMEIHQALTRSDRITNVLCRHEQGEIFAAEGYA 156
34/V. carteri       PRKGADILIQCLEREGVDNVFAYPGGASMEIHQALTRSDRITNVLCRHEQGEIFSAEGYA 155
35/C. variabilis    ARKGSDILVQALEREGVDTLFAYPGGASMEIHQALTRSDSIRNILCRHEQGEIFAAEGYA 103
1/P.  incisa        PRKGADILVQCLEREGAFRVFAYPGGASMEIHQALTRSGIIRNILCRHEQGEIFAAEGYA 180
                    .***:***:*.*****.  :*****************.  * *:**********:*****
33/C. reinhardtii   KAAGRVGVCIATSGPGATNLVTGLADAMMDSIPLVAITGQVPRRMIGTDAFQETPIVEVT 216
34/V. carteri       KASGRVGVCIATSGPGATNLVTRLDDAMMDSITLIAITGQVPRRMIGTDAFQETPIVEVT 215
35/C. variabilis    KVTGRVGVCIATSGPGATNLVTGLADALLDSVPLVAITGQVPRKLIGSDAFQETPIVEVT 163
1/P.  incisa        KCTGDVGVCIATSGPGATNLVTGLADAMLDSVPLVAITGQVPRKMIGTDGFQETPIVEVT 240
                    * :* **************** * **::**:.*:.*********::**:*.**********
33/C. reinhardtii   RAITKHNYLVLDIKDLPRVIKEAFYLARTGRPGPVLVDVPKDIQQQLAVPDWEAPMSITG 276
34/V. carteri       RAITKHNYLVLDIKDLPRVIKEAFYLARTGRPGPVLVDVPKDIQQQLAVPDWDSPMSITG 275
35/C. variabilis    RQITKHNFLVMDVKDIPRIIKEAFYLARTGRPGPVLVDVPKDVQQTLDVPDWDSPMTISA 223
1/P.  incisa        RQITKHNFLVMDLDDLPRIMKEAFYLARTGRPGPVLVDVPKDIQQQLAVPDWDTPMAISG 300
                    * *****:**:*:.*:**::*********************:** * ****::**:*:.
33/C. reinhardtii   YISRLPPPVEESQVLPVLRALQGAAKPVIYYGGGCLDAQAELREFAARTGIPLASTFMGL 336
34/V. carteri       YISRLPPPVEEYKMIPVLRAIQSATKPIIYYGGGCLDARNELREFAARTGIPLASKFMGL 335
35/P. incisa        YMSRLPAPPNPSQLAAVVRALKEAKRPTLYVGGGALDSSAELREFVRLTGIPVAQTLMGL 360
1/C.  variabilis    YMSRLPPPPQEAQLQQVLDAIRGSKRPALYVGGGCVDSAAEVIEFVQHTGIPVAQTLMAL 283
                    *:****.* :   ::  *: *::: :* :* ***.:*: *:  *:. **:**:*.::*.*
33/C. reinhardtii   GVVPSTDPNHLQMLGMHGTVFANYAVDQADLLVALGVRFDDRVTGKLDAFAARARIVHID 396
34/V. carteri       GVVPAEDPNHLQMLGMHGTVAANYAVDQADLLVALGVRFDDRVTGRLDAFASRARIVHVD 395
35/C. variabilis    GSFPEQDPLALQMLGMHGTVAANFAVNEADLLLAFGARFDDRVTGKLEAFAANARIVHID 343
1/P.  incisa        GTFPEEDPLALQMLGMHGTVYANYAVNDSDLLLAFGVRFDDRVTGKLEAFASRACIVHID 420
                    * .*  **  ********** **:**::**:*:*:*.*******:*:***:.* ***:*
33/C. reinhardtii   IDAAEISKNKTAHVPVCGDVKQALSHLNRLLAAEPLPADKWAGWRAELAAKRAEFPMRYP 456
34/V. carteri       IDAAEISKNKTAHVPVCGDVKQALRHLNRMLEAEPL-SDRFVAWRAELAAKRAEFPLRYP 454
35/C. variabilis    IDPAEIHKNKDAHIPVCADIKPALQILNRLLSQTPMDRSGYADWVAEVMAMKEENPLAYP 403
1/P.  incisa        IDPAEICKNKEAHIPICADLRASLIALNELLRRDPLPEGAFADWRAAIEAKKQEFPMTFP 480
                    **.*** *** **:*:*.*:: :*  **.:*   *:    *: * *   *  * * * *:*
33/C. reinhardtii   QRDDAIVPQHAIQVLGEETQGEAIITTGVGQHQMWAAQWYPYKETRRWISSGGLGSMGFG 516
34/V. carteri       QRDDAIVPQYAIQVLGEETKGEVIITTGVGQHQMWAAQWYPYKEPRRWISSGGLGSMGFG 514
35/C. variabilis    QHDDVIMPQWAIEVLYEESKGDAIITTGVGQHQMWAAQYYKFREPRRWATSGGLGSMGFG 463
1/P.  incisa        ERDDVIIPQRAIQMLYEETNGEAIISTGVGQHQMWAAQWYQYNEPRRWVTSGGLGSMGFG 540
                    ::**.*:** **::* **:.*:.**:*************:* :.*.*** :**********
33/C. reinhardtii   LPAALG-AAVAFDGKNGRPKKTVVDIDGDGSFLMNVQELATIFIEKLDVKVMLLNNQHLG 575
34/V. carteri       LPAALG-AAVAFDGKQGREKRIVVDIDGDGSFLMNVQELATVFIEKLDVKVMILNNQHLG 573
35/C. variabilis    LPSALG-AAAAFDGRDGRPSKLVVDIDGDGSFIMNCQELATASVEQLGTKVFILNNQYLG 522
1/P.  incisa        LPSALGAAAVAYDGTDGRPKKVVVDIDGDGSFLMNCQELATAAVEGLETKIMILNNQHLG 600
                    **:*** **.*:** :** .* ********:***.**** :* * .*::****:**
33/C. reinhardtii   MVVQWEDRFYKANRAHTYLGKRESEWHATQDEEDIYPNFVNMAQAFGVPSRRVIVKEQLR 635
34/V. carteri       MVVQWEDRFYKANRAHTYLGKREAEWHATGDEEDIYPNFVGMARSFGVPSMRVIRKEDLR 633
35/C. variabilis    MVMQWEDRFYKANRAHTYLGRREGEYQVTGNVQDIFPDFVKMADAFKVPAKRVTHPSELR 582
1/P.  incisa        MVVQWEDRFYKANRAHTYLGHRANEYHTTLDESHIFPDFVMMAKSCGVPGRRVIKPEELR 660
                    **:*****************:*  *:::.* : ..*:*:** ** :   **.  **  .:**
33/C. reinhardtii   GAIRTMLDTPGPYLLEVMVPHIEHVLPMIPGGASFKDIITEGDGTVKY-- 683
34/V. carteri       GANRTMLDTPGPYLLEVMVPHIEHVLPMIPGGATFKDIITEGDGSVKY-- 681
35/C. variabilis    AAIREMLDTPGPYLLDVMVPHIQHVLPMIPGGGSFKDIITKGDGTDVYFV 632
1/ P. incisa        GAIREMLDTPGPFLLDVMVPHVEHVLPMIPGGGSFKDIITKGDGRDEY-- 708
                   .* * *******:**:*****::*********.:******:***    *
```

Figure 2 agaggggcatcaaaaccagggaaacagcctcgcgcaaaccagcaacaattgtgagcagcgctgtttgcggctgtgtgagtgctcggtcgctctgtggggcaggtgcttcc
actatcacattatcatgagattgccctgccatccctgctcctctctgccacgctgggcgagaaggagctgtcgaaatcgcctccaggagtggccgtgactgcgatcgagttg
acgttagcacctgaatagtggtactggcacttcagagatagctgcaggtcagcatgcaaggcaccatgcggccgacggctggagcactgcagcagaccgtcggctgctg
gcacgtcccggccggcatcccccacgcacagcaggtgtttcaagttgttaggtggtgataagtgcctactgaagattcctttatgcagctgaacgaggcagcgtcccttgct
tcccagatcaacagccccttgtcactggtctgacaaaacgtgtgtgacaccctgacctgcgcatgcaggcgctgcgaggccgtatactgcccgaggagctgaagcagcgg
tgttcagcaaccaaacctaggtacaattgcagcagtagctcgacatgcatacacgcttaacgcagctgctggcagcagtctcgtgcctactgcttgccgccgcagcatggg
ctggctaccactacccttgaaacacacacaaggctcacaaaggtcctccctttcgtcccttgaggcagatgtgacgcctgctttgaccctgtgcacagggcggccaggcag
tcagcggtgaccgctgccaagcttgcagagggcaaggcaggcacaccatcacggagcttgcggcagcagccggcagcgccgcagcagcagcagcagcagcannnnn
nnnnnnnnnnnnnnnnnnnnnnnnnnnnaggtcgtctggcacgggtggcaggtggcacgctcttcaggcacttggtttggacaccctagcagtatgtcgtcgagt
tcagATGGAAGTCCTAGTACAGTGTGAGgtcagcgttggcaagcctgccttgtcaatgtggcacactgatgcctttgcgcagcacatgcggatggggtggagt
gtcgcatgagctggcatggtccagttggaccctgctggggatgctgctagtatgggttgctggaccagatgaccctggtcttgagtggtgaccatggcgccagtgcatcca
actgctggtgtggtttgcttctgccccagctgtcaagctactgcaggccgggcggtgcaggcaaaacaccaggcagtacatgtagcagcttgacggcagttgtagtagctc
accgccaccaatagtttgacgcactggcagactacctcagggcatgcctgcagctgctgtggcaagagggcatgagcctatccaatgcagctgctgtgaccacacatacc
tggcctgtctgtgcagCTGGTGGCGTTGCGGGAGGCTGCCAAGGCCTCGCTCTCATCCCCCGCGCCAGCCGAGTGGGTGGATCGGTTT
GGGTCGGAGCCCCGCAAGGGCGCGGATATCCTGGTGCAGTGCCTGGAGCGCGAGGGGGCCTTCCGCGTGTTTGCCTACCCCGG
CGGCGCCAGCATGGAGATCCATCAGGCCTTGACGCGCAGCGGCATCATCCGCAACATCCTGTGCCGCCATGAGCAGgtggggatgga
ccagactggcctggtgtggggcgaacaagtaggaaccagtgggccacggcacaggcggtacacatgcgtatggcatgggaggctgatagtgctcgcatgtagggatgg
cattttgcctgccaaagggcttggctatgcttgtgatgcacagtgggcctgcatctgagcactgaagccagtcagtcattggctgattgatgaatgccgcttcacccagtga
cagatgcattggcctcgggtgtggttcaaagctacagcaactgaaggacgctgagggcatgtgcatgtccaccaccttcacttactgtcaagtcttgcctacccatgcctga
tccagcatgaacgccatgtcgcagGGCGAGATCTTTGCGGCGGAGGGCTATGCCAAGTGCACGGGCGATGTGGGCGTGTGCATCGCGAC
CAGCGGGCCCGGCGCCACCAACCTCGTGACTGGCCTGGCTGATGCCATGCTGGACAGCGTTCCGCTTGTTGCCATCACAGGGCAG
gtgtgcacgcaagtcatcctgttgtttctcggcctgcctgtatggtctgtagcctgtttcaggtgctctgctcagcatcgcagatgcctcactgctttctgttgtggcgggggtc
actaacctgcataaagtttccaccttgagcagtcgttcaagcactactacttgtactgacagtcaacaatgagtccactgatcaggctacgaatgcaatgtggcggctgctc
gaccacatgtcagcgctctggcagtaaaccggggttccgcatgcaggTGCCCCGCAAGATGATCGGCACGGACGGGTTCCAGGAGACGCCGATTG
TGGAGGTGACGCGGCAGATCACCAAGCACAACTTCCTGGTCATGGACCTGGATGACCTGCCGCGCATCATGAAGGAGGtaggtgtg
gttcacctgcaacagaagcaaggcaatgtgcttgcacagcctgctcttctgcgcacagcagtccctgctgattgcttgtttggaagctaggcaacagctgctgcagacgca
caagcaacatcacatgcagaggcatcacacgcgattttggcaacctgccggctaggtggcctaatcctgactctctatcaccctgtctgtttttgcaggCATTCTACCTG
GCGCGCACGGGGCGGCCGGGCCCGGTGCTGGTGGATGTGCCCAAGGACATCCAGCAGCAGCTGGCGGtgccggactgggacacgccc
atggccatcagcggctacatgtcgcgcctgccnnnnnnnnnnnnnnnnnnnnnnnnnnnnnnnnnnnnncccgcctaacccctcacagctggccgcggtcgtgcgcgc
gctgaaggaggtacgcatgggtgatgcgcagcctcggtcgcctttctgaagtagacagcacgacctcagcgacgatcctcttcagttgagccgtgcccatgcatgcatgta
agtgcatggatgcaagcatgctgaatcgctttctgagacagactgtgcatgctatgggcaaggtacatcattaatggaaagttgctgctagctgcaagcctgcgaaccggc
cccgctttcaccagcgtttggtcgccttcagcacagtgcacctgtccatacggaacgcttctttcccacatcatgcacggtgcatcatgcacggtacaatcaagctgtctggc
gtgataaggagccgtggctgacatctcggcaggaaacttatgctttccccacttcctgtaggCTAAGAGGCCGACGCTGTACGTGGGCGGTGGCGCGCT
CGACTCGAGCGCTGAGCTGCGCGAGTTTGTGCGGCTGACGGGCATCCCCGTCGCGCAGACGCTTATGGGCCTGGGCACCTTCCC
CGAGGAAGACCCGCTGGCACTGCAGgtaggcttccttgctggcgggagactggtaacaaaggagggagcagtttgtgagcctatgggtgcgggacagtgcg
agatctggttgaatgatgtgttgtcatgcggcttgtgacacgttgtggcacctgcggcagctggatgccatcttatgggcagccatggcaccagcgcgtggggctatgggtc
atgctgacaaggccagtgccattgttttggatgcagATGCTGGGCATGCACGGTACGGTGTACGCCAACTACGCCGTCAACGACAGCGACCTG
CTGCTGGCGTTTGGCGTGCGCTTCGACGACCGCGTGACTGGCAAGCTGGAGGCGTTTGCTTCGCGCGCGCGCATCGTGCACATC
GACATCGACCCTGCGGAGATCTGCAAGAACAAGGAGGCCCACATACCCATCTGTGCAGgttggttcgtatagagcagcacccattttgttttcg
atgtcagtgcaaatgctagaaagccagttttgacagccagcacctcatgcagggctatgtatacttgcatactcagggcccgactgggcatgttgactgccaggttccttac
tgctcatgttggctgcagACCTGCGTGCGTCGTTGATAGCGCTGAATGAGCTGTTGCGGCGAGACCCTCTGCCAGAGGGCGCCTTTGCG
GACTGGCGGGCGGCCATTGAGGCCAAGAAGCAGGAGTTCCCCATGACCTTCCCGGAGCGGGACGACGTGATCATCCCACAGCGT
GCCATCCAGGTGAGAGGCGATGTCATGGATTCAgtgagacagccgcaagacatgttggcatgacatgttttcctctctgttctcttgctgggaatgtcattgt
ttgcgagcaggccacatctgcaagcaaaaccgtcttgcttgcctcgtgcagATGCTGTATGAGGAGACAAACGGCGAGGCCATCATCAGCACCGGC
GTGGGCCAGCACCAGATGTGGGCGGCGCAGTGGTACCAGTACAACGAGCCGCGGAGATGGGTCACGTCCGGCGGCCTCGGCTC
CATGGGCTTTGGCCTGCCATCCGCCCTCGGCGCGGCGGTGGCCTACGACGGCACGGACGGTCGGCCCAAGAAGGTatccgtcatatg
gaatcctctggctgaatggcatgcctttttttaaactctgcctggtatctgggtgaaagcgggtgaaagcgatgtctggccctacaaggagttggcgtgccactagaaatgc

Figure 7A ctgtgatagcaccaatctctgtttggagagagttcattgttgtatgaaggatacggggcaacccttgatccatgtacatacatgtctgtatgtgccctcgctgtttgaccggtc
aggtgagcgtgcatggtgctgcactgggctacccagtgcagagggatgtaggctgccatctgtgttcgtctagccgtgacgcgttttgtcaatgtatcatcagctggcgggt
atggcaaccaaagatggtaagcttggatgatgagggtgacctgttacctgacccagcgctctggcaaggcccttcatcatccagcgttactctactggctacattggttcag
tggcggacggtgtatctgctaggttgtgcacaccagtcagccagatgctggtagggcaattggttgtcctcctatgagccaacgacgacctttgctgatcgggtgtcaccct
gacgcaggcttgaccatgaagtctaagtagacgatgctgcttttcgcacacctctgctcaataaaatatgtggttggcatatgtgcatggccaagtgtgcggcatgaccag
ctgtctataaggccccgacatagctggcctttgttaggctgacgcctcatgaggttgctgccatcatcttgaccgctcacatggtatgacgacggttatgacgacggttatga
cgacggttatggcacgtggttgagcgtggtcaggtcctcgcatcacactacaatctttacatgcagatgctgtgtgcctatttgtgtgttatggagatagcatcgacggcag
gccagcagcctacaaggcagcggggactaaagcagtggatctggtgaccttgcttcgtagttgccactaccaggcaatagcaacatggggatcttgcagttgcaaggctc
agcttgtgactcaatctcgggcattgcgtccaatcttgtgcaggcgaggtggacgtggacatctaagtgtatgcttgctgacctgctaaaagtgtctgagtagaagcagtga
atatccgacgtggcatcaaggagtgagccgccttgtcgcgcaggtcgtcgtggacatcgatgatggccacagcttctgaagattcgcacacagcatcctgttggaacatga
ggcttgcctgcgcaggtGGTGGTGGACATCGACGGCGACGGCAGTTTCCTGATGAACTGCCAGGAGCTGGCGACGGCGGCGGTGGAG
GGCCTGGAGACCAAGATCATGATCCTCAACAACCAGCACCTGGGCATGGTGGTCCAGTGGGAGGACCGCTTCTACAAGGCCAAC
CGCGCACACACCTACCTCGGCCACCGGGtgcgtcccacaggctgctggtcttgccggtttcggtccagctgacttgttgtgacgctgttattgctggtgctgtgt
gagactgacatgaagttgctcttgcaagaggttggggcagagtggcagtgaaaaataagttgcaggcttcaaaccacgcaatgcatgcaggCCAATGAGTACCAC
ACGACGCTGGACGAGAGCCACATCTTCCCCGACTTTGTCATGATGGCCAAGTCGTGCGGCGTCCCAGGCCGGCGCGTCATCAAGC
CCGAGGAGCTGCGCGGGGCCATCaggtgggggctgctgccacgggcgcagtgcttgcagcatgcacactgtctgcaacttggtgaaccctggctgtggtgtgt
ggagatggcacattaagcacgtgcatcgcactgctgctgccaccctacaggtggagtccctctgctcttgctgcgctcgtcgcactggtggaagctcagcagctctattcct
gcagcagctgctgaagtgatgtgtctccactgacaGGGAGATGCTGGACACGCCCGGCCCCTTCCTGCTGGACGTGATGGTGCCGCATGTGG
AGCACGTGCTGCCCATGATCCCGGGCGGCGGCTCCTTCAAGGACATCATCACCAAGGGCGACGGCCGCGACGAGTACTAAggcgc
aggtcgcataggttgccatgggcaaggggctgccatggttgacttggtcgtgaccgatggttgtctgtccggacgttttcggtaacgtcctgcgctgtcctgctaccaaggtg
ctgtgctgtaggcacacaatgggcctggtatgg (SEQ ID NO: 28)

Figure 7B

```
                              SEQUENCE LISTING


<160> NUMBER OF SEQ ID NOS: 35

<210> SEQ ID NO 1
<211> LENGTH: 708
<212> TYPE: PRT
<213> ORGANISM: Parietochloris incisa

<400> SEQUENCE: 1

Met Gln Gly Thr Met Arg Pro Thr Ala Gly Ala Leu Gln Gln Thr Val
1               5                   10                  15

Gly Cys Trp His Val Pro Ala Gly Ile Pro His Ala Gln Gln Ala Leu
            20                  25                  30

Arg Gly Arg Ile Leu Pro Glu Glu Leu Lys Gln Arg Cys Ser Ala Thr
        35                  40                  45

Lys Pro Arg Ala Ala Arg Gln Ser Ala Val Thr Ala Ala Lys Leu Ala
    50                  55                  60

Glu Gly Lys Ala Gly Thr Pro Ser Arg Ser Leu Arg Gln Gln Pro Ala
65                  70                  75                  80

Ala Pro Gln Gln Gln Gln Gln Gln Gln Asp Ser Asn Glu Leu Val Ala
                85                  90                  95

Leu Arg Glu Ala Ala Lys Ala Ser Leu Ser Ser Pro Ala Pro Ala Glu
            100                 105                 110

Trp Val Asp Arg Phe Gly Ser Glu Pro Arg Lys Gly Ala Asp Ile Leu
        115                 120                 125

Val Gln Cys Leu Glu Arg Glu Gly Ala Phe Arg Val Phe Ala Tyr Pro
    130                 135                 140

Gly Gly Ala Ser Met Glu Ile His Gln Ala Leu Thr Arg Ser Gly Ile
145                 150                 155                 160

Ile Arg Asn Ile Leu Cys Arg His Glu Gln Gly Glu Ile Phe Ala Ala
                165                 170                 175
```

-continued

```
Glu Gly Tyr Ala Lys Cys Thr Gly Asp Val Gly Val Cys Ile Ala Thr
            180                 185                 190

Ser Gly Pro Gly Ala Thr Asn Leu Val Thr Gly Leu Ala Asp Ala Met
        195                 200                 205

Leu Asp Ser Val Pro Leu Val Ala Ile Thr Gly Gln Val Pro Arg Lys
    210                 215                 220

Met Ile Gly Thr Asp Gly Phe Gln Glu Thr Pro Ile Val Glu Val Thr
225                 230                 235                 240

Arg Gln Ile Thr Lys His Asn Phe Leu Val Met Asp Leu Asp Asp Leu
                245                 250                 255

Pro Arg Ile Met Lys Glu Ala Phe Tyr Leu Ala Arg Thr Gly Arg Pro
            260                 265                 270

Gly Pro Val Leu Val Asp Val Pro Lys Asp Ile Gln Gln Gln Leu Ala
        275                 280                 285

Val Pro Asp Trp Asp Thr Pro Met Ala Ile Ser Gly Tyr Met Ser Arg
    290                 295                 300

Leu Pro Ala Pro Pro Asn Pro Ser Gln Leu Ala Ala Val Val Arg Ala
305                 310                 315                 320

Leu Lys Glu Ala Lys Arg Pro Thr Leu Tyr Val Gly Gly Gly Ala Leu
                325                 330                 335

Asp Ser Ser Ala Glu Leu Arg Glu Phe Val Arg Leu Thr Gly Ile Pro
            340                 345                 350

Val Ala Gln Thr Leu Met Gly Leu Gly Thr Phe Pro Glu Glu Asp Pro
        355                 360                 365

Leu Ala Leu Gln Met Leu Gly Met His Gly Thr Val Tyr Ala Asn Tyr
    370                 375                 380

Ala Val Asn Asp Ser Asp Leu Leu Leu Ala Phe Gly Val Arg Phe Asp
385                 390                 395                 400

Asp Arg Val Thr Gly Lys Leu Glu Ala Phe Ala Ser Arg Ala Cys Ile
                405                 410                 415

Val His Ile Asp Ile Asp Pro Ala Glu Ile Cys Lys Asn Lys Glu Ala
            420                 425                 430

His Ile Pro Ile Cys Ala Asp Leu Arg Ala Ser Leu Ile Ala Leu Asn
        435                 440                 445

Glu Leu Leu Arg Arg Asp Pro Leu Pro Glu Gly Ala Phe Ala Asp Trp
    450                 455                 460

Arg Ala Ala Ile Glu Ala Lys Lys Gln Glu Phe Pro Met Thr Phe Pro
465                 470                 475                 480

Glu Arg Asp Asp Val Ile Ile Pro Gln Arg Ala Ile Gln Met Leu Tyr
                485                 490                 495

Glu Glu Thr Asn Gly Glu Ala Ile Ile Ser Thr Gly Val Gly Gln His
            500                 505                 510

Gln Met Trp Ala Ala Gln Trp Tyr Gln Tyr Asn Glu Pro Arg Arg Trp
        515                 520                 525

Val Thr Ser Gly Gly Leu Gly Ser Met Gly Phe Gly Leu Pro Ser Ala
    530                 535                 540

Leu Gly Ala Ala Ala Val Ala Tyr Asp Gly Thr Asp Gly Arg Pro Lys
545                 550                 555                 560

Lys Val Val Val Asp Ile Asp Gly Asp Gly Ser Phe Leu Met Asn Cys
                565                 570                 575

Gln Glu Leu Ala Thr Ala Ala Val Glu Gly Leu Glu Thr Lys Ile Met
            580                 585                 590
```

-continued

```
Ile Leu Asn Asn Gln His Leu Gly Met Val Val Gln Trp Glu Asp Arg
        595                 600                 605

Phe Tyr Lys Ala Asn Arg Ala His Thr Tyr Leu Gly His Arg Ala Asn
    610                 615                 620

Glu Tyr His Thr Thr Leu Asp Glu Ser His Ile Phe Pro Asp Phe Val
625                 630                 635                 640

Met Met Ala Lys Ser Cys Gly Val Pro Gly Arg Arg Val Ile Lys Pro
                645                 650                 655

Glu Glu Leu Arg Gly Ala Ile Arg Glu Met Leu Asp Thr Pro Gly Pro
            660                 665                 670

Phe Leu Leu Asp Val Met Val Pro His Val Glu His Val Leu Pro Met
        675                 680                 685

Ile Pro Gly Gly Gly Ser Phe Lys Asp Ile Ile Thr Lys Gly Asp Gly
    690                 695                 700

Arg Asp Glu Tyr
705


<210> SEQ ID NO 2
<211> LENGTH: 708
<212> TYPE: PRT
<213> ORGANISM: Parietochloris incisa

<400> SEQUENCE: 2

Met Gln Gly Thr Met Arg Pro Thr Ala Gly Ala Leu Gln Gln Thr Val
1               5                   10                  15

Gly Cys Trp His Val Pro Ala Gly Ile Pro His Ala Gln Gln Ala Leu
            20                  25                  30

Arg Gly Arg Ile Leu Pro Glu Glu Leu Lys Gln Arg Cys Ser Ala Thr
        35                  40                  45

Lys Pro Arg Ala Ala Arg Gln Ser Ala Val Thr Ala Ala Lys Leu Ala
    50                  55                  60

Glu Gly Lys Ala Gly Thr Pro Ser Arg Ser Leu Arg Gln Gln Pro Ala
65                  70                  75                  80

Ala Pro Gln Gln Gln Gln Gln Gln Gln Asp Ser Asn Glu Leu Val Ala
                85                  90                  95

Leu Arg Glu Ala Ala Lys Ala Ser Leu Ser Ser Pro Ala Pro Ala Glu
            100                 105                 110

Trp Val Asp Arg Phe Gly Ser Glu Pro Arg Lys Gly Ala Asp Ile Leu
        115                 120                 125

Val Gln Cys Leu Glu Arg Glu Gly Ala Phe Arg Val Phe Ala Tyr Pro
    130                 135                 140

Gly Gly Ala Ser Met Glu Ile His Gln Ala Leu Thr Arg Ser Gly Ile
145                 150                 155                 160

Ile Arg Asn Ile Leu Cys Arg His Glu Gln Gly Glu Ile Phe Ala Ala
                165                 170                 175

Glu Gly Tyr Ala Lys Cys Thr Gly Asp Val Gly Val Cys Ile Ala Thr
            180                 185                 190

Ser Gly Pro Gly Ala Thr Asn Leu Val Thr Gly Leu Ala Asp Ala Met
        195                 200                 205

Leu Asp Ser Val Pro Leu Val Ala Ile Thr Gly Gln Val Pro Arg Lys
    210                 215                 220

Met Ile Gly Thr Asp Gly Phe Gln Glu Thr Pro Ile Val Glu Val Thr
225                 230                 235                 240

Arg Gln Ile Thr Lys His Asn Phe Leu Val Met Asp Leu Asp Asp Leu
                245                 250                 255
```

-continued

```
Pro Arg Ile Met Lys Glu Ala Phe Tyr Leu Ala Arg Thr Gly Arg Pro
            260                 265                 270

Gly Pro Val Leu Val Asp Val Pro Lys Asp Ile Gln Gln Gln Leu Ala
        275                 280                 285

Val Pro Asp Trp Asp Thr Pro Met Ala Ile Ser Gly Tyr Met Ser Arg
    290                 295                 300

Leu Pro Ala Pro Pro Asn Pro Ser Gln Leu Ala Ala Val Val Arg Ala
305                 310                 315                 320

Leu Lys Glu Ala Lys Arg Pro Thr Leu Tyr Val Gly Gly Gly Ala Leu
                325                 330                 335

Asp Ser Ser Ala Glu Leu Arg Glu Phe Val Arg Leu Thr Gly Ile Pro
            340                 345                 350

Val Ala Gln Thr Leu Met Gly Leu Gly Thr Phe Pro Glu Glu Asp Pro
        355                 360                 365

Leu Ala Leu Gln Met Leu Gly Met His Gly Thr Val Tyr Ala Asn Tyr
    370                 375                 380

Ala Val Asn Asp Ser Asp Leu Leu Leu Ala Phe Gly Val Arg Phe Asp
385                 390                 395                 400

Asp Arg Val Thr Gly Lys Leu Glu Ala Phe Ala Ser Arg Ala Cys Ile
                405                 410                 415

Val His Ile Asp Ile Asp Pro Ala Glu Ile Cys Lys Asn Lys Glu Ala
            420                 425                 430

His Ile Pro Ile Cys Ala Asp Leu Arg Ala Ser Leu Ile Ala Leu Asn
        435                 440                 445

Glu Leu Leu Arg Arg Asp Pro Leu Pro Glu Gly Ala Phe Ala Asp Trp
    450                 455                 460

Arg Ala Ala Ile Glu Ala Lys Lys Gln Glu Phe Pro Met Thr Phe Pro
465                 470                 475                 480

Glu Arg Asp Asp Val Ile Ile Pro Gln Arg Ala Ile Gln Met Leu Tyr
                485                 490                 495

Glu Glu Thr Asn Gly Glu Ala Ile Ile Ser Thr Gly Val Gly Gln His
            500                 505                 510

Gln Met Trp Ala Ala Gln Trp Tyr Gln Tyr Asn Glu Pro Arg Arg Trp
        515                 520                 525

Val Thr Ser Gly Gly Leu Gly Ser Met Gly Phe Gly Leu Pro Ser Ala
    530                 535                 540

Leu Gly Ala Ala Ala Val Ala Tyr Asp Gly Thr Asp Gly Arg Pro Lys
545                 550                 555                 560

Lys Val Val Val Asp Ile Asp Gly Asp Gly Ser Phe Leu Met Asn Cys
                565                 570                 575

Gln Glu Leu Ala Thr Ala Ala Val Glu Gly Leu Glu Thr Lys Ile Met
            580                 585                 590

Ile Leu Asn Asn Gln His Leu Gly Met Val Val Gln Ser Glu Asp Arg
        595                 600                 605

Phe Tyr Lys Ala Asn Arg Ala His Thr Tyr Leu Gly His Arg Ala Asn
    610                 615                 620

Glu Tyr His Thr Thr Leu Asp Glu Ser His Ile Phe Pro Asp Phe Val
625                 630                 635                 640

Met Met Ala Lys Ser Cys Gly Val Pro Gly Arg Arg Val Ile Lys Pro
                645                 650                 655

Glu Glu Leu Arg Gly Ala Ile Arg Glu Met Leu Asp Thr Pro Gly Pro
            660                 665                 670
```

-continued

```
Phe Leu Leu Asp Val Met Val Pro His Val Glu His Val Leu Pro Met
        675                 680                 685

Ile Pro Gly Gly Gly Ser Phe Lys Asp Ile Ile Thr Lys Gly Asp Gly
    690                 695                 700

Arg Asp Glu Tyr
705


<210> SEQ ID NO 3
<211> LENGTH: 2124
<212> TYPE: DNA
<213> ORGANISM: Parietochloris Incisa

<400> SEQUENCE: 3

atgcaaggca ctatgcggcc gacggctgga gcactgcagc agaccgtcgg ctgctggcac     60

gtcccggccg gcatccccca cgcacagcag gcgctgcgag gccgtatact gcccgaggag    120

ctgaagcagc ggtgttcagc aaccaaacct agggcggcca ggcagtcagc ggtgaccgct    180

gccaagcttg cagagggcaa ggcaggcaca ccatcacgga gcttgcggca gcagccggca    240

gcgccgcagc agcagcagca gcagcaggat agcaatgagc tggtggcgtt gcgggaggct    300

gccaaggcct cgctctcatc ccccgcgcca gccgagtggg tggatcggtt tgggtcggag    360

ccccgcaagg gcgcggatat cctggtgcag tgcctggagc gcgagggggc cttccgcgtg    420

tttgcctacc ccggcggcgc cagcatggag atccatcagg ccttgacgcg cagcggcatc    480

atccgcaaca tcctgtgccg ccatgagcag ggcgagatct ttgcggcgga gggctatgcc    540

aagtgcacgg gcgatgtggg cgtgtgcatc gcgaccagcg ggcccggcgc caccaacctc    600

gtgactggcc tggctgatgc catgctggac agcgttccgc ttgttgccat cacagggcag    660

gtgccccgca agatgatcgg cacggacggg ttccaggaga cgccgattgt ggaggtgacg    720

cggcagatca ccaagcacaa cttcctggtc atggacctgg atgacctgcc gcgcatcatg    780

aaggaggcat tctacctggc gcgcacgggg cggccgggcc cggtgctggt ggatgtgccc    840

aaggacatcc agcagcagct ggcggtgccg gactgggaca cgcccatggc catcagcggc    900

tacatgtcgc gcctgccggc cccgcctaac ccctcacagc tggccgcggt cgtgcgcgcg    960

ctgaaggagg ctaagaggcc gacgctgtac gtgggcggtg gcgcgctcga ctcgagcgct   1020

gagctgcgcg agtttgtgcg gctgacgggc atccccgtcg cgcagacgct tatgggcctg   1080

ggcaccttcc ccgaggaaga cccgctggca ctgcagatgc tgggcatgca cggtacggtg   1140

tacgccaact acgccgtcaa cgacagcgac ctgctgctgg cgtttggcgt gcgcttcgac   1200

gaccgcgtga ctggcaagct ggaggcgttt gcttcgcgcg cgtgcatcgt gcacatcgac   1260

atcgaccctg cggagatctg caagaacaag gaggcccaca tacccatctg tgcagacctg   1320

cgtgcgtcgt tgatagcgct gaatgagctg ttgcggcgag accctctgcc agagggcgcc   1380

tttgcggact ggcgggcggc cattgaggcc aagaagcagg agttccccat gaccttcccg   1440

gagcgggacg acgtgatcat cccacagcgt gccatccaga tgctgtatga ggagacaaac   1500

ggcgaggcca tcatcagcac cggcgtgggc cagcaccaga tgtgggcggc gcagtggtac   1560

cagtacaacg agccgcggag atgggtcacg tccggcggcc tcggctccat gggctttggc   1620

ctgccatccg ccctcggcgc ggcggtggcc tacgacggca cggacggtcg gcccaagaag   1680

gtggtggtgg acatcgacgg cgacggcagt ttcctgatga actgccagga gctggcgacg   1740

gcggcggtgg agggcctgga gaccaagatc atgatcctca acaaccagca cctgggcatg   1800

gtggtccagt gggaggaccg cttctacaag gccaaccgcg cacacaccta cctcggccac   1860
```

-continued cgggccaatg agtaccacac gacgctggac gagagccaca tcttccccga ctttgtcatg 1920
atggccaagt cgtgcggcgt cccaggccgg cgcgtcatca agcccgagga gctgcgcggg 1980
gccatcaggg agatgctgga cacgcccggc cccttcctgc tggacgtgat ggtgccgcat 2040
gtggagcacg tgctgcccat gatcccgggc ggcggctcct tcaaggacat catcaccaag 2100
ggcgacggcc gcgacgagta ctaa 2124

<210> SEQ ID NO 4
<211> LENGTH: 2124
<212> TYPE: DNA
<213> ORGANISM: Parietochloris Incisa

<400> SEQUENCE: 4
atgcaaggca ctatgcggcc gacggctgga gcactgcagc agaccgtcgg ctgctggcac 60
gtcccggccg gcatcccccca cgcacagcag gcgctgcgag gccgtatact gcccgaggag 120
ctgaagcagc ggtgttcagc aaccaaacct agggcggcca ggcagtcagc ggtgaccgct 180
gccaagcttg cagagggcaa ggcaggcaca ccatcacgga gcttgcggca gcagccggca 240
gcgccgcagc agcagcagca gcagcaggat agcaatgagc tggtggcgtt gcgggaggct 300
gccaaggcct cgctctcatc ccccgcgcca gccgagtggg tggatcggtt tgggtcggag 360
ccccgcaagg gcgcggatat cctggtgcag tgcctggagc gcgagggggc cttccgcgtg 420
tttgcctacc ccggcggcgc cagcatggag atccatcagg ccttgacgcg cagcggcatc 480
atccgcaaca tcctgtgccg ccatgagcag ggcgagatct ttgcggcgga gggctatgcc 540
aagtgcacgg gcgatgtggg cgtgtgcatc gcgaccagcg ggcccggcgc caccaacctc 600
gtgactggcc tggctgatgc catgctggac agcgttccgc ttgttgccat cacagggcag 660
gtgccccgca agatgatcgg cacggacggg ttccaggaga cgccgattgt ggaggtgacg 720
cggcagatca ccaagcacaa cttcctggtc atggacctgg atgacctgcc gcgcatcatg 780
aaggaggcat tctacctggc gcgcacgggg cggccgggcc cggtgctggt ggatgtgccc 840
aaggacatcc agcagcagct ggcggtgccg gactgggaca cgcccatggc catcagcggc 900
tacatgtcgc gcctgccggc cccgcctaac ccctcacagc tggccgcggt cgtgcgcgcg 960
ctgaaggagg ctaagaggcc gacgctgtac gtgggcggtg gcgcgctcga ctcgagcgct 1020
gagctgcgcg agtttgtgcg gctgacgggc atccccgtcg cgcagacgct tatgggcctg 1080
ggcaccttcc ccgaggaaga cccgctggca ctgcagatgc tgggcatgca cggtacggtg 1140
tacgccaact acgccgtcaa cgacagcgac ctgctgctgg cgtttggcgt gcgcttcgac 1200
gaccgcgtga ctggcaagct ggaggcgttt gcttcgcgcg cgtgcatcgt gcacatcgac 1260
atcgaccctg cggagatctg caagaacaag gaggcccaca tacccatctg tgcagacctg 1320
cgtgcgtcgt tgatagcgct gaatgagctg ttgcggcgag accctctgcc agagggcgcc 1380
tttgcggact ggcgggcggc cattgaggcc aagaagcagg agttccccat gaccttcccg 1440
gagcgggacg acgtgatcat cccacagcgt gccatccaga tgctgtatga ggagacaaac 1500
ggcgaggcca tcatcagcac cggcgtgggc cagcaccaga tgtgggcggc gcagtggtac 1560
cagtacaacg agccgcggag atgggtcacg tccggcggcc tcggctccat gggctttggc 1620
ctgccatccg ccctcggcgc ggcggtggcc tacgacggca cggacggtcg gcccaagaag 1680
gtggtggtgg acatcgacgg cgacggcagt ttcctgatga actgccagga gctggcgacg 1740
gcggcggtgg agggcctgga gaccaagatc atgatcctca acaaccagca cctgggcatg 1800
gtggtccagt cggaggaccg cttctacaag gccaaccgcg cacacaccta cctcggccac 1860

-continued cgggccaatg agtaccacac gacgctggac gagagccaca tcttccccga ctttgtcatg 1920
atggccaagt cgtgcggcgt cccaggccgg cgcgtcatca agcccgagga gctgcgcggg 1980
gccatcaggg agatgctgga cacgcccggc cccttcctgc tggacgtgat ggtgccgcat 2040
gtggagcacg tgctgcccat gatcccgggc ggcggctcct tcaaggacat catcaccaag 2100
ggcgacggcc gcgacgagta ctaa 2124

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
aaccggcgca cacgtacctg g 21

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
cggggatcat gggcagcacg 20

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
ggcaccgagc ttcagaac 18

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
acggtgcctg catccacat 19

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
agatcaccaa gcacaacttc ct 22

<210> SEQ ID NO 10
<211> LENGTH: 22
<212> TYPE: DNA
<213> ORGANISM: Artificial Sequence
<220> FEATURE:
<223> OTHER INFORMATION: Primer -continued

<400> SEQUENCE: 10
atgacaaagt cggggaagat gt 22

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
acgctggacg agagccacat cttc 24

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
ccctgtgatg gcaacaagcg gaac 24

<210> SEQ ID NO 13
<211> LENGTH: 27
<212> TYPE: DNA
<213> ORGANISM: Artificial Sequence
<220> FEATURE:
<223> OTHER INFORMATION: Primer

<400> SEQUENCE: 13
atagtcgaca gcatgcaagg cactatg 27

<210> SEQ ID NO 14
<211> LENGTH: 26
<212> TYPE: DNA
<213> ORGANISM: Artificial Sequence
<220> FEATURE:
<223> OTHER INFORMATION: Primer

<400> SEQUENCE: 14
aatgtcgacc tgcgccttag tactcg 26

<210> SEQ ID NO 15
<211> LENGTH: 33
<212> TYPE: DNA
<213> ORGANISM: Artificial Sequence
<220> FEATURE:
<223> OTHER INFORMATION: Primer

<400> SEQUENCE: 15
gcatggtggt ccagtcggag gaccgcttct aca 33

<210> SEQ ID NO 16
<211> LENGTH: 33
<212> TYPE: DNA
<213> ORGANISM: Artificial Sequence
<220> FEATURE:
<223> OTHER INFORMATION: Primer

<400> SEQUENCE: 16
tgtagaagcg gtcctccgac tggaccacca tgc 33

<210> SEQ ID NO 17
<211> LENGTH: 30

<212> TYPE: DNA
<213> ORGANISM: Artificial Sequence
<220> FEATURE:
<223> OTHER INFORMATION: Primer

<400> SEQUENCE: 17
tatagtcgac gcgcaaaagg aatataaaaa 30

<210> SEQ ID NO 18
<211> LENGTH: 29
<212> TYPE: DNA
<213> ORGANISM: Artificial Sequence
<220> FEATURE:
<223> OTHER INFORMATION: Primer

<400> SEQUENCE: 18
tataggatcc catagttagt tccccgtcc 29

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
ggatccatgc aaggcactat g 21

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
ggatccaatg agctggtggc 20

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
gtcgacctgc gccttagtac tc 22

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
agaggggcat caaaaccagg 20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23

-continued cgtagttggc gtacaccgta 20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
cctcagcgac gatcctcttc 20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
ccataccagg cccattgtgt 20

<210> SEQ ID NO 26
<211> LENGTH: 39
<212> TYPE: DNA
<213> ORGANISM: Artificial Sequence
<220> FEATURE:
<223> OTHER INFORMATION: Primer

<400> SEQUENCE: 26
ctgggcatgg tggtccagtc ggaggaccgc ttctacaag 39

<210> SEQ ID NO 27
<211> LENGTH: 39
<212> TYPE: DNA
<213> ORGANISM: Artificial Sequence
<220> FEATURE:
<223> OTHER INFORMATION: Primer

<400> SEQUENCE: 27
cttgtagaag cggtcctccg actggaccac catgcccag 39

<210> SEQ ID NO 28
<211> LENGTH: 6896
<212> TYPE: DNA
<213> ORGANISM: Parietochloris incisa
<220> FEATURE:
<221> NAME/KEY: misc_feature
<222> LOCATION: (877)..(909)
<223> OTHER INFORMATION: n is a, c, g, or t
<220> FEATURE:
<221> NAME/KEY: misc_feature
<222> LOCATION: (2934)..(2966)
<223> OTHER INFORMATION: n is a, c, g, or t

<400> SEQUENCE: 28
agaggggcat caaaaccagg gaaacagcct cgcgcaaacc agcaacaatt gtgagcagcg 60
ctgtttgcgg ctgtgtgagt gctcggtcgc tctgtggggc aggtgcttcc actatcacat 120
tatcatgaga ttgccctgcc atccctgctc ctctctgcca cgctgggcga gaaggagctg 180
tcgaaatcgc ctccaggagt ggccgtgact gcgatcgagt tgacgttagc acctgaatag 240
tggtactggc acttcagaga tagctgcagg tcagcatgca aggcaccatg cggccgacgg 300
ctggagcact gcagcagacc gtcggctgct ggcacgtccc ggccggcatc ccccacgcac 360
agcaggtgtt tcaagttgtt aggtggtgat aagtgcctac tgaagattcc tttatgcagc 420

-continued

```
tgaacgaggc agcgtccctt gcttcccaga tcaacagccc cttgtcactg gtctgacaaa    480
acgtgtgtga caccctgacc tgcgcatgca ggcgctgcga ggccgtatac tgcccgagga    540
gctgaagcag cggtgttcag caaccaaacc taggtacaat tgcagcagta gctcgacatg    600
catacacgct taacgcagct gctggcagca gtctcgtgcc tactgcttgc cgccgcagca    660
tgggctggct accactaccc ttgaaacaca cacaaggctc acaaaggtcc tccctttcgt    720
cccttgaggc agatgtgacg cctgctttga ccctgtgcac agggcggcca ggcagtcagc    780
ggtgaccgct gccaagcttg cagagggcaa ggcaggcaca ccatcacgga gcttgcggca    840
gcagccggca gcgccgcagc agcagcagca gcagcannnn nnnnnnnnnn nnnnnnnnnn    900
nnnnnnnnna ggtcgtctgg cacgggtggc aggtggcacg ctcttcaggc acttggtttg    960
gacaccctag cagtatgtcg tcgagttcag atggaagtcc tagtacagtg tgaggtcagc   1020
gttggcaagc ctgccttgtc aatgtggcac actgatgcct ttgcgcagca catgcggatg   1080
gggtggagtg tcgcatgagc tggcatggtc cagttggacc ctgctgggga tgctgctagt   1140
atgggttgct ggaccagatg accctggtct tgagtggtga ccatggcgcc agtgcatcca   1200
actgctggtg tggtttgctt ctgccccagc tgtcaagcta ctgcaggccg ggcggtgcag   1260
gcaaaacacc aggcagtaca tgtagcagct tgacggcagt tgtagtagct caccgccacc   1320
aatagtttga cgcactggca gactacctca gggcatgcct gcagctgctg tggcaagagg   1380
gcatgagcct atccaatgca gctgctgtga ccacacatac ctggcctgtc tgtgcagctg   1440
gtggcgttgc gggaggctgc caaggcctcg ctctcatccc ccgcgccagc cgagtgggtg   1500
gatcggtttg ggtcggagcc ccgcaagggc gcggatatcc tggtgcagtg cctggagcgc   1560
gagggggcct tccgcgtgtt tgcctacccc ggcggcgcca gcatggagat ccatcaggcc   1620
ttgacgcgca gcggcatcat ccgcaacatc ctgtgccgcc atgagcaggt ggggatggac   1680
cagactggcc tggtgtgggg cgaacaagta ggaaccagtg ggccacggca caggcggtac   1740
acatgcgtat ggcatgggag gctgatagtg ctcgcatgta gggatggcat tttgcctgcc   1800
aaagggcttg gctatgcttg tgatgcacag tgggcctgca tctgagcact gaagccagtc   1860
agtcattggc tgattgatga atgccgcttc acccagtgac agatgcattg gcctcgggtg   1920
tggttcaaag ctacagcaac tgaaggacgc tgagggcatg tgcatgtcca ccaccttcac   1980
ttactgtcaa gtcttgccta cccatgcctg atccagcatg aacgccatgt cgcagggcga   2040
gatctttgcg gcggagggct atgccaagtg cacgggcgat gtgggcgtgt gcatcgcgac   2100
cagcgggccc ggcgccacca acctcgtgac tggcctggct gatgccatgc tggacagcgt   2160
tccgcttgtt gccatcacag ggcaggtgtg cacgcaagtc atcctgttgt ttctcggcct   2220
gcctgtatgg tctgtagcct gtttcaggtg ctctgctcag catcgcagat gcctcactgc   2280
tttctgttgt ggcgggggtc actaacctgc ataaagtttc caccttgagc agtcgttcaa   2340
gcactactac ttgtactgac agtcaacaat gagtccactg atcaggctac gaatgcaatg   2400
tggcggctgc tcgaccacat gtcagcgctc tggcagtaaa ccggggttcc gcatgcaggt   2460
gccccgcaag atgatcggca cggacgggtt ccaggagacg ccgattgtgg aggtgacgcg   2520
gcagatcacc aagcacaact tcctggtcat ggacctggat gacctgccgc gcatcatgaa   2580
ggaggtaggt gtggttcacc tgcaacagaa gcaaggcaat gtgcttgcac agcctgctct   2640
tctgcgcaca gcagtccctg ctgattgctt gtttggaagc taggcaacag ctgctgcaga   2700
cgcacaagca acatcacatg cagaggcatc acacgcgatt ttggcaacct gccggctagg   2760
```

-continued

```
tggcctaatc ctgactctct atcaccctgt ctgtttttgc aggcattcta cctggcgcgc   2820
acggggcggc cgggcccggt gctggtggat gtgcccaagg acatccagca gcagctggcg   2880
gtgccggact gggacacgcc catggccatc agcggctaca tgtcgcgcct gccnnnnnnn   2940
nnnnnnnnnn nnnnnnnnnn nnnnnncccg cctaacccct cacagctggc cgcggtcgtg   3000
cgcgcgctga aggaggtacg catgggtgat gcgcagcctc ggtcgccttt ctgaagtaga   3060
cagcacgacc tcagcgacga tcctcttcag ttgagccgtg cccatgcatg catgtaagtg   3120
catggatgca agcatgctga atcgctttct gagacagact gtgcatgcta tgggcaaggt   3180
acatcattaa tggaaagttg ctgctagctg caagcctgcg aaccggcccc gctttcacca   3240
gcgtttggtc gccttcagca cagtgcacct gtccatacgg aacgcttctt tcccacatca   3300
tgcacggtgc atcatgcacg gtacaatcaa gctgtctggc gtgataagga gccgtggctg   3360
acatctcggc aggaaactta tgctttcccc acttcctgta ggctaagagg ccgacgctgt   3420
acgtgggcgg tggcgcgctc gactcgagcg ctgagctgcg cgagtttgtg cggctgacgg   3480
gcatccccgt cgcgcagacg cttatgggcc tgggcacctt ccccgaggaa gacccgctgg   3540
cactgcaggt aggcttcctt gctggcggga gactggtaac aaaggaggga gcagtttgtg   3600
agcctatggg tgcgggacag tgcgagatct ggttgaatga tgtgttgtca tgcggcttgt   3660
gacacgttgt ggcacctgcg gcagctggat gccatcttat gggcagccat ggcaccagcg   3720
cgtggggcta tgggtcatgc tgacaaggcc agtgccattg ttttggatgc agatgctggg   3780
catgcacggt acggtgtacg ccaactacgc cgtcaacgac agcgacctgc tgctggcgtt   3840
tggcgtgcgc ttcgacgacc gcgtgactgg caagctggag gcgtttgctt cgcgcgcgcg   3900
catcgtgcac atcgacatcg accctgcgga gatctgcaag aacaaggagg cccacatacc   3960
catctgtgca ggttggttcg tatagagcag cacccatttt gttttcgatg tcagtgcaaa   4020
tgctagaaag ccagttttga cagccagcac ctcatgcagg gctatgtata cttgcatact   4080
cagggcccga ctgggcatgt tgactgccag gttccttact gctcatgttg gctgcagacc   4140
tgcgtgcgtc gttgatagcg ctgaatgagc tgttgcggcg agaccctctg ccagagggcg   4200
cctttgcgga ctggcgggcg gccattgagg ccaagaagca ggagttcccc atgaccttcc   4260
cggagcggga cgacgtgatc atcccacagc gtgccatcca ggtgagaggc gatgtcatgg   4320
attcagtgag acagccgcaa gacatgttgg catgacatgt tttcctctct gttctcttgc   4380
tgggaatgtc attgtttgcg agcaggccac atctgcaagc aaaaccgtct tgcttgcctc   4440
gtgcagatgc tgtatgagga gacaaacggc gaggccatca tcagcaccgg cgtgggccag   4500
caccagatgt gggcggcgca gtggtaccag tacaacgagc cgcggagatg ggtcacgtcc   4560
ggcggcctcg gctccatggg ctttggcctg ccatccgccc tcggcgcggc ggtggcctac   4620
gacggcacgg acggtcggcc caagaaggta tccgtcatat ggaatcctct ggctgaatgg   4680
catgcctttt tttaaactct gcctggtatc tgggtgaaag cgggtgaaag cgatgtctgg   4740
ccctacaagg agttggcgtg ccactagaaa tgcctgtgat agcaccaatc tctgtttgga   4800
gagagttcat tgttgtatga aggatacggg gcaacccttg atccatgtac atacatgtct   4860
gtatgtgccc tcgctgtttg accggtcagg tgagcgtgca tggtgctgca ctgggctacc   4920
cagtgcagag ggatgtaggc tgccatctgt gttcgtctag ccgtgacgcg ttttgtcaat   4980
gtatcatcag ctggcgggta tggcaaccaa agatggtaag cttggatgat gagggtgacc   5040
tgttacctga cccagcgctc tggcaaggcc cttcatcatc cagcgttact ctactggcta   5100
cattggttca gtggcggacg gtgtatctgc taggttgtgc acaccagtca gccagatgct   5160
```

```
ggtagggcaa ttggttgtcc tcctatgagc caacgacgac ctttgctgat cgggtgtcac   5220
cctgacgcag gcttgaccat gaagtctaag tagacgatgc tgcttttcgc acacctctgc   5280
tcaataaaat atgtggttgg catatgtgca tggccaagtg tgcggcatga ccagctgtct   5340
ataaggcccc gacatagctg gcctttgtta ggctgacgcc tcatgaggtt gctgccatca   5400
tcttgaccgc tcacatggta tgacgacggt tatgacgacg gttatgacga cggttatggc   5460
acgtggttga gcgtggtcag gtcctcgcat cacactacaa tctttacatg cagatgctgt   5520
gtgcctattt gtgtgttatg gagatagcat cgacggcagg ccagcagcct acaaggcagc   5580
ggggactaaa gcagtggatc tggtgacctt gcttcgtagt tgccactacc aggcaatagc   5640
aacatgggga tcttgcagtt gcaaggctca gcttgtgact caatctcggg cattgcgtcc   5700
aatcttgtgc aggcgaggtg gacgtggaca tctaagtgta tgcttgctga cctgctaaaa   5760
gtgtctgagt agaagcagtg aatatccgac gtggcatcaa ggagtgagcc gccttgtcgc   5820
gcaggtcgtc gtggacatcg atgatggcca cagcttctga agattcgcac acagcatcct   5880
gttggaacat gaggcttgcc tgcgcaggtg gtggtggaca tcgacggcga cggcagtttc   5940
ctgatgaact gccaggagct ggcgacggcg gcggtggagg gcctggagac caagatcatg   6000
atcctcaaca accagcacct gggcatggtg gtccagtggg aggaccgctt ctacaaggcc   6060
aaccgcgcac acacctacct cggccaccgg gtgcgtccca caggctgctg gtcttgccgg   6120
tttcggtcca gctgacttgt tgtgacgctg ttattgctgg tgctgtgtga gactgacatg   6180
aagttgctct tgcaagaggt tggggcagag tggcagtgaa aaataagttg caggcttcaa   6240
accacgcaat gcatgcaggc caatgagtac cacacgacgc tggacgagag ccacatcttc   6300
cccgactttg tcatgatggc caagtcgtgc ggcgtcccag gccggcgcgt catcaagccc   6360
gaggagctgc gcggggccat caggtggggg ctgctgccac gggcgcagtg cttgcagcat   6420
gcacactgtc tgcaacttgg tgaaccctgg ctgtggtgtg tggagatggc acattaagca   6480
cgtgcatcgc actgctgctg ccaccctaca ggtggagtcc ctctgctctt gctgcgctcg   6540
tcgcactggt ggaagctcag cagctctatt cctgcagcag ctgctgaagt gatgtgtctc   6600
cactgacagg gagatgctgg acacgcccgg cccccttcctg ctggacgtga tggtgccgca   6660
tgtggagcac gtgctgccca tgatcccggg cggcggctcc ttcaaggaca tcatcaccaa   6720
gggcgacggc cgcgacgagt actaaggcgc aggtcgcata ggttgccatg ggcaaggggc   6780
tgccatggtt gacttggtcg tgaccgatgg ttgtctgtcc ggacgttttc ggtaacgtcc   6840
tgcgctgtcc tgctaccaag gtgctgtgct gtaggcacac aatgggcctg gtatgg        6896
```

<210> SEQ ID NO 29
<211> LENGTH: 10
<212> TYPE: PRT
<213> ORGANISM: Chlamydomonas reinhardtii

<400> SEQUENCE: 29

```
Ile Gly Thr Asp Ala Phe Gln Glu Thr Pro
1               5                   10
```

<210> SEQ ID NO 30
<211> LENGTH: 8
<212> TYPE: PRT
<213> ORGANISM: Chlamydomonas reinhardtii

<400> SEQUENCE: 30

```
Met Leu Gly Met His Gly Thr Val
```

```
1               5


<210> SEQ ID NO 31
<211> LENGTH: 7
<212> TYPE: PRT
<213> ORGANISM: Chlamydomonas reinhardtii

<400> SEQUENCE: 31

Arg Ala His Thr Tyr Leu Gly
1               5


<210> SEQ ID NO 32
<211> LENGTH: 6
<212> TYPE: PRT
<213> ORGANISM: Chlamydomonas reinhardtii

<400> SEQUENCE: 32

Val Leu Pro Met Ile Pro
1               5


<210> SEQ ID NO 33
<211> LENGTH: 682
<212> TYPE: PRT
<213> ORGANISM: Chlamydomonas reinhardtii

<400> SEQUENCE: 33

Lys Ala Leu Arg Ser Gly Thr Ala Val Ala Arg Gly Gln Ala Gly Cys
1               5                   10                  15

Val Ser Pro Ala Pro Arg Pro Val Pro Met Ser Ser Gln Ala Met Ile
            20                  25                  30

Pro Ser Thr Ser Ser Pro Ala Ala Arg Ala Pro Ala Arg Ser Gly Arg
        35                  40                  45

Arg Ala Leu Ala Val Ser Ala Lys Leu Ala Asp Gly Ser Arg Arg Met
    50                  55                  60

Gln Ser Glu Glu Val Arg Arg Ala Lys Glu Val Ala Gln Ala Ala Leu
65                  70                  75                  80

Ala Lys Asp Ser Pro Ala Asp Trp Val Asp Arg Tyr Gly Ser Glu Pro
                85                  90                  95

Arg Lys Gly Ala Asp Ile Leu Val Gln Ala Leu Glu Arg Glu Gly Val
            100                 105                 110

Asp Ser Val Phe Ala Tyr Pro Gly Gly Ala Ser Met Glu Ile His Gln
        115                 120                 125

Ala Leu Thr Arg Ser Asp Arg Ile Thr Asn Val Leu Cys Arg His Glu
    130                 135                 140

Gln Gly Glu Ile Phe Ala Ala Glu Gly Tyr Ala Lys Ala Ala Gly Arg
145                 150                 155                 160

Val Gly Val Cys Ile Ala Thr Ser Gly Pro Gly Ala Thr Asn Leu Val
                165                 170                 175

Thr Gly Leu Ala Asp Ala Met Met Asp Ser Ile Pro Leu Val Ala Ile
            180                 185                 190

Thr Gly Gln Val Pro Arg Arg Met Ile Gly Thr Asp Ala Phe Gln Glu
        195                 200                 205

Thr Pro Ile Val Glu Val Thr Arg Ala Ile Thr Lys His Asn Tyr Leu
    210                 215                 220

Val Leu Asp Ile Lys Asp Leu Pro Arg Val Ile Lys Glu Ala Phe Tyr
225                 230                 235                 240

Leu Ala Arg Thr Gly Arg Pro Gly Pro Val Leu Val Asp Val Pro Lys
                245                 250                 255
```

```
Asp Ile Gln Gln Gln Leu Ala Val Pro Asp Trp Glu Ala Pro Met Ser
            260                 265                 270

Ile Thr Gly Tyr Ile Ser Arg Leu Pro Pro Pro Val Glu Glu Ser Gln
        275                 280                 285

Val Leu Pro Val Leu Arg Ala Leu Gln Gly Ala Ala Lys Pro Val Ile
    290                 295                 300

Tyr Tyr Gly Gly Gly Cys Leu Asp Ala Gln Ala Glu Leu Arg Glu Phe
305                 310                 315                 320

Ala Ala Arg Thr Gly Ile Pro Leu Ala Ser Thr Phe Met Gly Leu Gly
                325                 330                 335

Val Val Pro Ser Thr Asp Pro Asn His Leu Gln Met Leu Gly Met His
            340                 345                 350

Gly Thr Val Phe Ala Asn Tyr Ala Val Asp Gln Ala Asp Leu Leu Val
        355                 360                 365

Ala Leu Gly Val Arg Phe Asp Asp Arg Val Thr Gly Lys Leu Asp Ala
    370                 375                 380

Phe Ala Ala Arg Ala Arg Ile Val His Ile Asp Ile Asp Ala Ala Glu
385                 390                 395                 400

Ile Ser Lys Asn Lys Thr Ala His Val Pro Val Cys Gly Asp Val Lys
                405                 410                 415

Gln Ala Leu Ser His Leu Asn Arg Leu Leu Ala Ala Glu Pro Leu Pro
            420                 425                 430

Ala Asp Lys Trp Ala Gly Trp Arg Ala Glu Leu Ala Ala Lys Arg Ala
        435                 440                 445

Glu Phe Pro Met Arg Tyr Pro Gln Arg Asp Asp Ala Ile Val Pro Gln
    450                 455                 460

His Ala Ile Gln Val Leu Gly Glu Glu Thr Gln Gly Glu Ala Ile Ile
465                 470                 475                 480

Thr Thr Gly Val Gly Gln His Gln Met Trp Ala Ala Gln Trp Tyr Pro
                485                 490                 495

Tyr Lys Glu Thr Arg Arg Trp Ile Ser Ser Gly Gly Leu Gly Ser Met
            500                 505                 510

Gly Phe Gly Leu Pro Ala Ala Leu Gly Ala Ala Val Ala Phe Asp Gly
        515                 520                 525

Lys Asn Gly Arg Pro Lys Lys Thr Val Val Asp Ile Asp Gly Asp Gly
    530                 535                 540

Ser Phe Leu Met Asn Val Gln Glu Leu Ala Thr Ile Phe Ile Glu Lys
545                 550                 555                 560

Leu Asp Val Lys Val Met Leu Leu Asn Asn Gln His Leu Gly Met Val
                565                 570                 575

Val Gln Trp Glu Asp Arg Phe Tyr Lys Ala Asn Arg Ala His Thr Tyr
            580                 585                 590

Leu Gly Lys Arg Glu Ser Glu Trp His Ala Thr Gln Asp Glu Glu Asp
        595                 600                 605

Ile Tyr Pro Asn Phe Val Asn Met Ala Gln Ala Phe Gly Val Pro Ser
    610                 615                 620

Arg Arg Val Ile Val Lys Glu Gln Leu Arg Gly Ala Ile Arg Thr Met
625                 630                 635                 640

Leu Asp Thr Pro Gly Pro Tyr Leu Leu Glu Val Met Val Pro His Ile
                645                 650                 655

Glu His Val Leu Pro Met Ile Pro Gly Gly Ala Ser Phe Lys Asp Ile
            660                 665                 670
```

-continued

```
Ile Thr Glu Gly Asp Gly Thr Val Lys Tyr
        675                 680


<210> SEQ ID NO 34
<211> LENGTH: 681
<212> TYPE: PRT
<213> ORGANISM: Volvox carteri

<400> SEQUENCE: 34

Met Ala Leu Arg Phe Cys Pro Thr Ala Ala Pro Pro Arg Gly Cys Gly
1               5                   10                  15

Thr Pro Ile Gln His Pro Val Leu Leu Leu Pro His Lys Ala Leu Leu
            20                  25                  30

Pro Tyr Ser Thr Ala Ala Ser Arg Gln Ala Ala Arg Pro Ala Arg Val
        35                  40                  45

Cys Val Thr Ala Tyr Ala Lys Leu Ala Asp Gly Ser Ala Arg Arg Met
    50                  55                  60

Gln Ser Glu Glu Val Arg Arg Ala Lys Glu Val Ala Gln Ala Ala Leu
65                  70                  75                  80

Ala Lys Glu Ser Pro Ala Asp Trp Val Asp Arg Phe Gly Ser Glu Pro
                85                  90                  95

Arg Lys Gly Ala Asp Ile Leu Ile Gln Cys Leu Glu Arg Glu Gly Val
            100                 105                 110

Asp Asn Val Phe Ala Tyr Pro Gly Gly Ala Ser Met Glu Ile His Gln
        115                 120                 125

Ala Leu Thr Arg Ser Asp Arg Ile Thr Asn Val Leu Cys Arg His Glu
    130                 135                 140

Gln Gly Glu Ile Phe Ser Ala Glu Gly Tyr Ala Lys Ala Ser Gly Arg
145                 150                 155                 160

Val Gly Val Cys Ile Ala Thr Ser Gly Pro Gly Ala Thr Asn Leu Val
                165                 170                 175

Thr Arg Leu Asp Asp Ala Met Met Asp Ser Ile Thr Leu Ile Ala Ile
            180                 185                 190

Thr Gly Gln Val Pro Arg Arg Met Ile Gly Thr Asp Ala Phe Gln Glu
        195                 200                 205

Thr Pro Ile Val Glu Val Thr Arg Ala Ile Thr Lys His Asn Tyr Leu
    210                 215                 220

Val Leu Asp Ile Lys Asp Leu Pro Arg Val Ile Lys Glu Ala Phe Tyr
225                 230                 235                 240

Leu Ala Arg Thr Gly Arg Pro Gly Pro Val Leu Val Asp Val Pro Lys
                245                 250                 255

Asp Ile Gln Gln Gln Leu Ala Val Pro Asp Trp Asp Ser Pro Met Ser
            260                 265                 270

Ile Thr Gly Tyr Ile Ser Arg Leu Pro Pro Pro Val Glu Glu Tyr Lys
        275                 280                 285

Met Ile Pro Val Leu Arg Ala Ile Gln Ser Ala Thr Lys Pro Ile Ile
    290                 295                 300

Tyr Tyr Gly Gly Gly Cys Leu Asp Ala Arg Asn Glu Leu Arg Glu Phe
305                 310                 315                 320

Ala Ala Arg Thr Gly Ile Pro Leu Ala Ser Lys Phe Met Gly Leu Gly
                325                 330                 335

Val Val Pro Ala Glu Asp Pro Asn His Leu Gln Met Leu Gly Met His
            340                 345                 350

Gly Thr Val Ala Ala Asn Tyr Ala Val Asp Gln Ala Asp Leu Leu Val
        355                 360                 365
```

-continued

Ala Leu Gly Val Arg Phe Asp Asp Arg Val Thr Gly Arg Leu Asp Ala
    370                 375                 380

Phe Ala Ser Arg Ala Arg Ile Val His Val Asp Ile Asp Ala Ala Glu
385                 390                 395                 400

Ile Ser Lys Asn Lys Thr Ala His Val Pro Val Cys Gly Asp Val Lys
                405                 410                 415

Gln Ala Leu Arg His Leu Asn Arg Met Leu Glu Ala Glu Pro Leu Ser
            420                 425                 430

Asp Arg Phe Val Ala Trp Arg Ala Glu Leu Ala Ala Lys Arg Ala Glu
        435                 440                 445

Phe Pro Leu Arg Tyr Pro Gln Arg Asp Asp Ala Ile Val Pro Gln Tyr
    450                 455                 460

Ala Ile Gln Val Leu Gly Glu Glu Thr Lys Gly Glu Val Ile Ile Thr
465                 470                 475                 480

Thr Gly Val Gly Gln His Gln Met Trp Ala Ala Gln Trp Tyr Pro Tyr
                485                 490                 495

Lys Glu Pro Arg Arg Trp Ile Ser Ser Gly Gly Leu Gly Ser Met Gly
            500                 505                 510

Phe Gly Leu Pro Ala Ala Leu Gly Ala Ala Val Ala Phe Asp Gly Lys
        515                 520                 525

Gln Gly Arg Glu Lys Arg Ile Val Val Asp Ile Asp Gly Asp Gly Ser
    530                 535                 540

Phe Leu Met Asn Val Gln Glu Leu Ala Thr Val Phe Ile Glu Lys Leu
545                 550                 555                 560

Asp Val Lys Val Met Ile Leu Asn Asn Gln His Leu Gly Met Val Val
                565                 570                 575

Gln Trp Glu Asp Arg Phe Tyr Lys Ala Asn Arg Ala His Thr Tyr Leu
            580                 585                 590

Gly Lys Arg Glu Ala Glu Trp His Ala Thr Gly Asp Glu Glu Asp Ile
        595                 600                 605

Tyr Pro Asn Phe Val Gly Met Ala Arg Ser Phe Gly Val Pro Ser Met
    610                 615                 620

Arg Val Ile Arg Lys Glu Asp Leu Arg Gly Ala Asn Arg Thr Met Leu
625                 630                 635                 640

Asp Thr Pro Gly Pro Tyr Leu Leu Glu Val Met Val Pro His Ile Glu
                645                 650                 655

His Val Leu Pro Met Ile Pro Gly Gly Ala Thr Phe Lys Asp Ile Ile
            660                 665                 670

Thr Glu Gly Asp Gly Ser Val Lys Tyr
        675                 680

<210> SEQ ID NO 35
<211> LENGTH: 632
<212> TYPE: PRT
<213> ORGANISM: Craspedia variabilis

<400> SEQUENCE: 35

Met Ala Lys Asp Phe Ser Asn Lys Ala Asn Lys Ala Ser Lys Ala Glu
1               5                   10                  15

Leu Glu Ala Ala Arg Gln Ala Ala Gln Ala Ser Leu Ala Ser Glu Pro
            20                  25                  30

Pro Val Glu Trp Val Asp Arg Phe Asn Gly Gln Ala Arg Lys Gly Ser
        35                  40                  45

Asp Ile Leu Val Gln Ala Leu Glu Arg Glu Gly Val Asp Thr Leu Phe

-continued

```
    50                  55                  60

Ala Tyr Pro Gly Gly Ala Ser Met Glu Ile His Gln Ala Leu Thr Arg
65                  70                  75                  80

Ser Asp Ser Ile Arg Asn Ile Leu Cys Arg His Glu Gln Gly Glu Ile
                85                  90                  95

Phe Ala Ala Glu Gly Tyr Ala Lys Val Thr Gly Arg Val Gly Val Cys
            100                 105                 110

Ile Ala Thr Ser Gly Pro Gly Ala Thr Asn Leu Val Thr Gly Leu Ala
        115                 120                 125

Asp Ala Leu Leu Asp Ser Val Pro Leu Val Ala Ile Thr Gly Gln Val
    130                 135                 140

Pro Arg Lys Leu Ile Gly Ser Asp Ala Phe Gln Glu Thr Pro Ile Val
145                 150                 155                 160

Glu Val Thr Arg Gln Ile Thr Lys His Asn Phe Leu Val Met Asp Val
                165                 170                 175

Lys Asp Ile Pro Arg Ile Ile Lys Glu Ala Phe Tyr Leu Ala Arg Thr
            180                 185                 190

Gly Arg Pro Gly Pro Val Leu Val Asp Val Pro Lys Asp Val Gln Gln
        195                 200                 205

Thr Leu Asp Val Pro Asp Trp Asp Ser Pro Met Thr Ile Ser Ala Tyr
    210                 215                 220

Met Ser Arg Leu Pro Pro Pro Pro Gln Glu Ala Gln Leu Gln Gln Val
225                 230                 235                 240

Leu Asp Ala Ile Arg Gly Ser Lys Arg Pro Ala Leu Tyr Val Gly Gly
                245                 250                 255

Gly Cys Val Asp Ser Ala Ala Glu Val Ile Glu Phe Val Gln His Thr
            260                 265                 270

Gly Ile Pro Val Ala Gln Thr Leu Met Ala Leu Gly Ser Phe Pro Glu
        275                 280                 285

Gln Asp Pro Leu Ala Leu Gln Met Leu Gly Met His Gly Thr Val Ala
    290                 295                 300

Ala Asn Phe Ala Val Asn Glu Ala Asp Leu Leu Leu Ala Phe Gly Ala
305                 310                 315                 320

Arg Phe Asp Asp Arg Val Thr Gly Lys Leu Glu Ala Phe Ala Ala Asn
                325                 330                 335

Ala Arg Ile Val His Ile Asp Ile Asp Pro Ala Glu Ile His Lys Asn
            340                 345                 350

Lys Asp Ala His Ile Pro Val Cys Ala Asp Ile Lys Pro Ala Leu Gln
        355                 360                 365

Ile Leu Asn Arg Leu Leu Ser Gln Thr Pro Met Asp Arg Ser Gly Tyr
    370                 375                 380

Ala Asp Trp Val Ala Glu Val Met Ala Met Lys Glu Glu Asn Pro Leu
385                 390                 395                 400

Ala Tyr Pro Gln His Asp Asp Val Ile Met Pro Gln Trp Ala Ile Glu
                405                 410                 415

Val Leu Tyr Glu Glu Ser Lys Gly Asp Ala Ile Ile Thr Thr Gly Val
            420                 425                 430

Gly Gln His Gln Met Trp Ala Ala Gln Tyr Tyr Lys Phe Arg Glu Pro
        435                 440                 445

Arg Arg Trp Ala Thr Ser Gly Gly Leu Gly Ser Met Gly Phe Gly Leu
    450                 455                 460

Pro Ser Ala Leu Gly Ala Ala Ala Ala Phe Asp Gly Arg Asp Gly Arg
465                 470                 475                 480
```

-continued

```
Pro Ser Lys Leu Val Val Asp Ile Asp Gly Asp Gly Ser Phe Ile Met
                485                 490                 495

Asn Cys Gln Glu Leu Ala Thr Ala Ser Val Glu Gln Leu Gly Thr Lys
            500                 505                 510

Val Phe Ile Leu Asn Asn Gln Tyr Leu Gly Met Val Met Gln Trp Glu
        515                 520                 525

Asp Arg Phe Tyr Lys Ala Asn Arg Ala His Thr Tyr Leu Gly Arg Arg
    530                 535                 540

Glu Gly Glu Tyr Gln Val Thr Gly Asn Val Gln Asp Ile Phe Pro Asp
545                 550                 555                 560

Phe Val Lys Met Ala Asp Ala Phe Lys Val Pro Ala Lys Arg Val Thr
                565                 570                 575

His Pro Ser Glu Leu Arg Ala Ala Ile Arg Glu Met Leu Asp Thr Pro
            580                 585                 590

Gly Pro Tyr Leu Leu Asp Val Met Val Pro His Ile Gln His Val Leu
        595                 600                 605

Pro Met Ile Pro Gly Gly Gly Ser Phe Lys Asp Ile Ile Thr Lys Gly
    610                 615                 620

Asp Gly Thr Asp Val Tyr Phe Val
625                 630
```

COMPOSITIONS AND METHODS FOR CONFERRING HERBICIDE RESISTANCE

REFERENCE TO CO-PENDING APPLICATIONS

Priority is claimed as a 371 of international application number PCT/IB2012/055347, filed on Oct. 4, 2012; which claims priority to U.S. provisional patent application Ser. No. 61/543,339, filed on Oct. 5, 2011.

FIELD OF THE INVENTION

The present invention provides a protein, specifically *Parietochloris incisa* acetohydroxyacid synthase, and methods for producing branched-chain amino acid in a cell. The present invention further provides polypeptides and polynucleotides useful for conferring herbicide resistance in a cell or an organism. In particular, the present invention discloses a mutated acetohydroxyacid synthase which is resistant to herbicides.

BACKGROUND OF THE INVENTION

Branched-chain amino acids (BCAAs), namely leucine, isoleucine and valine, are synthesized by plants, algae, fungi, bacteria and archaea, but not by animals. BCCAs are essential amino acids for humans and are used clinically for the treatment of burns and hepatic encephalopathy as well as for increasing muscle mass. The enzymes of the BCAA biosynthetic pathway are potential targets for the development of herbicides, fungicides, and antimicrobial compounds. Some of the most popular herbicides (e.g. sulfometuron methyl, SMM), act by inhibiting the first common enzyme in the BCAA biosynthetic pathway, acetohydroxyacid synthase (AHAS). Since AHAS is required for the synthesis of all three BCAAs, its inhibition is detrimental to the organism and effectively inhibits its growth. Plant and green algal AHAS are localized in the chloroplast and fungal AHAS in the mitochondria, although the genes may be present in the nuclear or organelle genome. In cases of nuclear-encoded genes, the enzyme is transported to the target subcellullar compartment by an additional, poorly conserved, N-terminal targeting peptide.

Microalgae are one of the richest sources of long-chain polyunsaturated fatty acids (LC-PUFAs). The green freshwater microalga *Parietochloris incisa* (Trebouxiophyceae) is the only microalga able to accumulate extraordinary high amounts of LC- PUFA arachidonic acid (ARA)-rich triacylglycerols (TAG). When *P. incisa* is cultivated under nitrogen starvation, the fatty acid (FA) content of the alga is over 35% of dry weight; ARA constitutes about 60% of total FAs, and over 90% of cell ARA is deposited in TAG, making it the richest green dietary source of ARA. LC-PUFAs include the ω3-fatty acids, eicosapentaenoic acid (EPA, 20:5ω3), docosahexaenoic acid (DHA, 22:6ω3), ω6-fatty acid, arachidonic acid (ARA, 20:4ω6) and dihomo-γ-linolenic acid (DGLA, 20:3ω6). LC-PUFA are major components of membrane phospholipids of the retina, brain and testis and are predominant in the human brain and breast milk (specifically ARA and DHA). ARA is necessary for normal fetal growth and for cognitive development in infants and is also the primary substrate in eicosanoids biosynthesis, which regulates many physiological processes such as homeostasis, reproduction, immune and inflammatory responses.

Use of antibiotic resistance genes as selection markers in transformation processes presents numerous environmental and health risks, as well as regulatory difficulties that define the organism as genetically modified (GM). Thus, a selection system based on mutation(s) of an endogenous gene(s) is highly advantageous. It has been reported that mutant forms of AHAS exhibit herbicide resistance in yeast, higher plants and green algae, where most of the characterized AHAS herbicide resistances is due to a single or double amino acid change from the wild-type enzyme sequence. At least 17 different amino acid substitutions in AHAS are known to confer resistance to growth inhibiting herbicides. For example, in tobacco, a resistant mutant with a single amino acid change of Tryptophan557, within a conserved region of AHAS, was found to be insensitive to inhibition by two sulfonylurea herbicides, chlorsulfuron and SMM. In addition, corresponding Trp residue mutations were shown to be important for AHAS SMM resistance of *Escherichia coli, Mycobacterium tuberculosis, Brassica napus* and the red microalga *Porphyridium* sp.

There remains an unmet need for the development of cells, in particular microalgal cells which are capable of producing LC-PUFA in large scale systems and which are resistant to herbicides, using methods which do not classify the organism as genetically modified.

SUMMARY OF THE INVENTION

According to one aspect, the present invention provides an isolated protein, comprising an amino acid sequence set forth in SEQ ID NO: 1.

According to one embodiment the present invention further provides a composition comprising the protein comprising an amino acid sequence set forth in SEQ ID NO: 1 and an acceptable carrier.

According to another embodiment the present invention further provides an isolated polynucleotide comprising a coding portion encoding the protein comprising the amino acid sequence set forth in SEQ ID NO: 1, wherein said coding portion comprises a nucleic acid sequence set forth in SEQ ID NO: 3.

According to yet another embodiment the present invention further provides an expression vector comprising said polynucleotide.

According to yet another embodiment the present invention further provides a cell transformed by said polynucleotide.

According to yet another embodiment the present invention provides a method for enhancing the production of branched-chain amino acid (BCAA) in a cell comprising the step of transforming a cell with said polynucleotide operably linked to a constitutive promoter, thereby increasing the production of BCAA in a cell.

According to yet another embodiment the cell is an alga cell.

According to yet another embodiment said method further comprises the step of transforming said cell with a polynucleotide encoding an enzyme selected from the group consisting of: Threonine deaminase (TD), ketol-acid Reductoisomerase (KARI), dihydroxyacid dehydratase (DHAD); transaminase (TA), 2-isopropylmalate synthase (2-IPMS), 3-isopropylmalate dehydratase (3-IPMD) and 3-isopropylmalate dehydrogenase (3-IPMDH), or a combination thereof.

According to another aspect, the present invention provides an isolated protein comprising an amino acid sequence set forth in SEQ ID NO: 2.

According to one embodiment, the present invention provides a composition comprising the protein comprising an amino acid sequence set forth in SEQ ID NO: 2 and an acceptable carrier.

According to another embodiment, the present invention further provides an isolated polynucleotide comprising a coding portion encoding the protein comprising an amino acid sequence set forth in SEQ ID NO: 1, wherein said coding portion comprises a nucleic acid sequence set forth in SEQ ID NO: 3.

According to yet another embodiment the present invention further provides an expression vector comprising said polynucleotide.

According to yet another embodiment, the present invention further provides a cell transformed by said polynucleotide.

According to yet another embodiment the present invention further provides a method for producing a cell having herbicide resistance comprising the step of transforming said cell with said polynucleotide, thereby producing a cell having herbicide resistance.

According to yet another embodiment said cell is an alga cell.

According to yet another embodiment, said alga is *Parietochloris incisa.*

According to yet another embodiment, said herbicide is selected from the group consisting of: sulfonylureas, imidazolinones, triazolopyrimidines and combinations thereof.

According to yet another embodiment, said alga produces long-chain polyunsaturated fatty acid (LC-PUFA), arachidonic acid (ARA) and rich triacylglycerols (TAG).

According to yet another embodiment, said method further comprises the step of transforming said alga with a polynucleotide encoding an enzyme involved in the biosynthesis of ω-3 LC-PUFA in said alga.

According to yet another embodiment said enzyme involved in the biosynthesis of ω-3 LC-PUFA is ω-3 desaturase, C20 PUFA elongase, Δ4 desaturase or combinations thereof.

According to yet another embodiment, said ω-3 LC-PUFA is eicosapentaenoic acid (EPA, 20:5 ω-3) or docosahexaenoic acid (DHA, 22:6 ω-3).

According to yet another embodiment, the present invention provides a method for producing an alga having an endogenous selection marker for herbicide resistance, comprising the step of transforming said alga with said polynucleotide comprising a coding portion encoding the protein comprising an amino acid sequence set forth in SEQ ID NO: 1, wherein said coding portion comprises a nucleic acid sequence set forth in SEQ ID NO: 3, thereby producing an alga having an endogenous selection marker for herbicide resistance.

According to one embodiment, said alga is *Parietochloris incisa.*

According to another embodiment, said herbicide inhibits acetohydroxyacid synthase.

Further embodiments, features, advantages and the full scope of applicability of the present invention will become apparent from the detailed description and drawings given hereinafter. However, it should be understood that the detailed description, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1. Is a multiple sequence alignment of known AHAS proteins. Alignment of five AHAS sequences from green algae (*C. reinhardtii, C. variabilis* and of *V. carteri*.), moss (*P. patens* subsp.) and higher plant (*B. napus*), showing the conserved "blocks" A-D, SEQ ID Nos: 29-32, accordingly, used for primer design.

FIG. 2. Provides multiple sequence alignment of PiAHAS with other green algae AHAS (*C. reinhardtii*, (SEQ ID NO: 33); *C. variabilis* (SEQ ID NO: 35); and of *V. carteri*. (SEQ ID NO: 34)). The poorly conserves N-terminus, is shown (grey highlight). The black triangle points to start of the "truncated" PiAHAS gene form. Mutated Tryptophan residue, involved in the herbicide binding and resistance, is shown as conserved (black highlight).

FIGS. 7A and 7B collectively disclose, and referred to as FIG. 7, the DNA sequence encoding the genomic fragment of *P. incisa*, containing AHAS gene. (1) Loci of mutation are bold letters with gray background and (2) region of primers annealing used for cloning are underlined. (3) CDS region labeled with capital letters. (4) Region of primers annealing used for mutation introduction is double underlined.

DETAILED DESCRIPTION OF THE INVENTION

Figure 3:
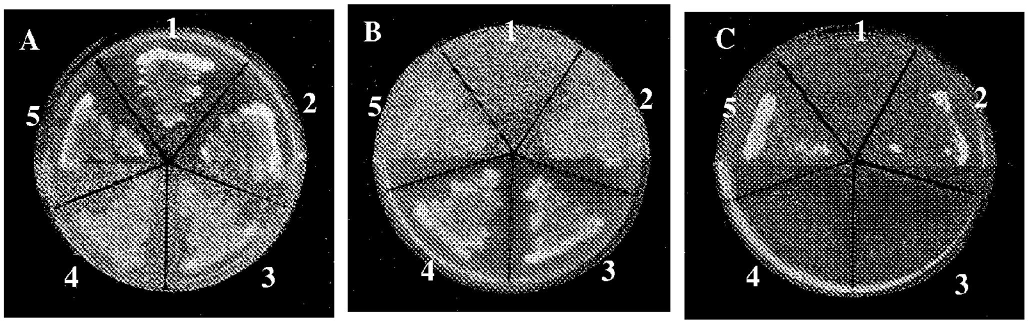
FIG. 3. Shows functional complementation of BUM1 by cloned PiAHAS genes. A single colony from each transformed cell lines was streaked onto M9 supplemented with valine, leucine and isoleucine (A), M9 (B) and M9 supplemented with 50 μM SMM (C) agar plates and incubated at 37° C. for 48 hrs. The sections are: 1. pEp-empty, 2. pAH29 (ilvGM), 3. pEp-ORF, 4. pEp-truncated and 5. pEp-mut.

In one aspect, the present invention provides an isolated protein. In one embodiment the present invention provides that the isolated protein is a polypeptide. In another embodiment, the present invention provides that the isolated protein is an enzyme. In another embodiment, the present invention provides that the isolated protein is acetohydroxyacid synthase (AHAS). In another embodiment, the present invention provides that the isolated protein is a microalgae AHAS. In another embodiment, the present invention provides that the isolated protein is *Parietochloris incisa* (Trebouxiophyceae) AHAS.

In another embodiment, the present invention provides an isolated acetohydroxyacid synthase (AHAS) comprising the amino acid sequence:

(SEQ ID NO: 1)

```
MQGTMRPTAGALQQTVGCWHVPAGIPHAQQALRGRILPEELKQRCSATKP
RAARQSAVTAAKLAEGKAGTPSRSLRQQPAAPQQQQQQQDSNELVALREA
AKASLSSPAPAEWVDRFGSEPRKGADILVQCLEREGAFRVFAYPGGASME
IHQALTRSGIIRNILCRHEQGEIFAAEGYAKCTGDVGVCIATSGPGATNL
VTGLADAMLDSVPLVAITGQVPRKMIGTDGFQETPIVEVTRQITKHNFLV
MDLDDLPRIMKEAFYLARTGRPGPVLVDVPKDIQQQLAVPDWDTPMAISG
YMSRLPAPPNPSQLAAVVRALKEAKRPTLYVGGGALDSSAELREFVRLTG
IPVAQTLMGLGTFPEEDPLALQMLGMHGTVYANYAVNDSDLLLAFGVRFD
DRVTGKLEAFASRACIVHIDIDPAEICKNKEAHIPICADLRASLIALNEL
LRRDPLPEGAFADWRAAIEAKKQEFPMTFPERDDVIIPQRAIQMLYEETN
GEAIISTGVGQHQMWAAQWYQYNEPRRWVTSGGLGSMGFGLPSALGAAAV
AYDGTDGRPKKVVVDIDGDGSFLMNCQELATAAVEGLETKIMILNNQHLG
MVVQWEDRFYKANRAHTYLGHRANEYHTTLDESHIFPDFVMMAKSCGVPG
RRVIKPEELRGAIREMLDTPGPFLLDVMVPHVEHVLPMIPGGGSFKDIIT
KGDGRDEY.
```

In another embodiment, the AHAS of the present invention comprises an amino acid sequence that is at least 60%, at least 70%, at least 80%, at least 85%, at least 90%, at least 95% or at least 98% homologous to the amino acid sequence of SEQ ID NO: 1. Each possibility represents a separate possibility of the invention.

In another embodiment, the AHAS of the present invention comprises an amino acid sequence that is at least 60%, at least 70%, at least 80%, at least 85%, at least 90%, at least 95% or at least 98% identical to the amino acid sequence of SEQ ID NO: 1. Each possibility represents a separate possibility of the invention.

In another embodiment, the AHAS as described herein comprises at least a portion of the amino acid shown in SEQ ID NO: 1. In another embodiment, the AHAS as described herein is a variant of SEQ ID NO: 1.

The term "variant" as used herein refers to a protein or a polypeptide which is derived from the sequence through the insertion or deletion of one or more amino acid residues or the substitution of one or more amino acid residues with amino acid residues having similar properties, e.g., the replacement of a polar amino acid residue with another polar amino acid residue, or the replacement of a non-polar amino acid residue with another non-polar amino acid residue. In all cases, variants must have an AHAS function as defined herein.

In another embodiment, the AHAS as described herein further comprises a leader peptide. In another embodiment, the leader peptide allows the polypeptide to be specifically localized or targeted to a target organelle within the cell (e.g. chloroplast and mitochondria). In another embodiment, the AHAS as described herein further comprises a chemical modification such as glycosylation that increases its stability. In another embodiment, the AHAS as described herein further comprises a peptide unrelated to AHAS which increases its stability.

In another embodiment, the present invention provides an isolated AHAS. In another embodiment, the present invention provides that the polypeptide has the function of synthesizing branched-chain amino acid. In another embodiment, the branched-chain amino acid is leucine, isoleucine and valine. Each possibility represents a separate embodiment of the invention.

In another embodiment, the present invention provides an isolated AHAS which catalyzes the synthesis of (2S)-acetolactate (AL) from two molecules of pyruvate. In another embodiment, the present invention provides an isolated AHAS which catalyzes the synthesis of (2S)-2-aceto-2-hydroxybutyrate (AHB) from pyruvate and 2-ketobutyrate. In another embodiment, the present in invention provides an isolated AHAS comprising the amino acid sequence of SEQ ID NO: 1.

In another embodiment, the present invention provides a protein comprising an AHAS activity. In another embodiment, the present invention provides that the protein of the invention is a recombinant AHAS.

In another embodiment, the present invention provides an isolated polynucleotide encoding the protein comprising the amino acid sequence set forth in SEQ ID NO: 1. In another embodiment, the isolated polynucleotide is an isolated DNA molecule. In another embodiment, the isolated polynucleotide is an isolated cDNA molecule. In another embodiment, the isolated polynucleotide comprises a DNA sequence encoding an AHAS as described herein. In another embodiment, the isolated polynucleotide comprises a DNA sequence encoding a polypeptide comprising an AHAS activity.

In another embodiment, the isolated polynucleotide comprises a DNA sequence comprising the sequence:

(SEQ ID NO: 3)

```
ATGCAAGGCACTATGCGGCCGACGGCTGGAGCACTGCAGCAGACCGTCGG
CTGCTGGCACGTCCCGGCCGGCATCCCCCACGCACAGCAGGCGCTGCGAG
GCCGTATACTGCCCGAGGAGCTGAAGCAGCGGTGTTCAGCAACCAAACCT
AGGGCGGCCAGGCAGTCAGCGGTGACCGCTGCCAAGCTTGCAGAGGGCAA
GGCAGGCACACCATCACGGAGCTTGCGGCAGCAGCCGGCAGCGCCGCAGC
AGCAGCAGCAGCAGCAGGATAGCAATGAGCTGGTGGCGTTGCGGGAGGCT
GCCAAGGCCTCGCTCTCATCCCCCGCGCCAGCCGAGTGGGTGGATCGGTT
TGGGTCGGAGCCCCGCAAGGGCGCGGATATCCTGGTGCAGTGCCTGGAGC
GCGAGGGGGCCTTCCGCGTGTTTGCCTACCCCGGCGGCGCCAGCATGGAG
ATCCATCAGGCCTTGACGCGCAGCGGCATCATCCGCAACATCCTGTGCCG
CCATGAGCAGGGCGAGATCTTTGCGGCGGCGGAGGGCTATGCCAAGTGCA
CGGATGTGGGCGTGTGCATCGCGACCAGCGGGCCCGGCGCCACCAACCTC
GTGACTGGCCTGGCTGATGCCATGCTGGACAGCGTTCCGCTTGTTGCCAT
CACAGGGCAGGTGCCCCGCAAGATGATCGGCACGGACGATGGGGTTCCAG
GAGACGCCGATTGTGGAGGTGACGCGGCAGATCACCAAGCACAACTTCCT
GGTCACCTGGATGACCTGCCGCGCATCATGAAGGAGGCATTCTACCTGGC
ACGGGGGCGCCGGCCGGGCCCGGTGCTGGTGGATGTGCCCAAGGACATCC
AGCAGCAGCTGGCGGTGCCGGACTGGGACACGCCCATGGCCATCAGCGGC
TACATGTCGCGCCTGCCGGCCCCGCCTAACCCCTCACAGCTGGCCGCGGT
CGTGCGCGCGCTGAAGGAGGCTAAGAGGCCGACGCTGTACGTGGGCGGTG
GCGCGCTCGACTCGAGCGCTGAGCTGCGCGAGTTTGTGCGGCTGACGGGC
CCCGCTATCCCCGTCGCGCAGACGCTTATGGGCCTGGGCACCTTCCCCGA
GGAAGAGGCACTGCAGATGCTGGGCATGCACGGTACGGTGTACGCCAACT
ACGCCGTCAACGACAGCGACCTGCTGCTGGCGTTTGGCGTGCGCTTCGAC
```

-continued

```
GACCGCGTGACTGGCAAGCTGGAGGCGTTTGCTTCGCGCGTGCATCGT

GCACATCGACATCGACCCTGCGGAGATCTGCAAGAACAAGGAGGCCCACA

TACCCATCTGTGCAGACCTGCGTGCGTCGTTGATAGCGCTGAATGAGCTG

TTGCGGCGAGACCCTCTGCCAGAGGGCGCCTTTGCGGACTGGCGGGCGGC

CATTGAGGCCAAGAAGCAGGAGTTCCCCATGACCTTCCCGGAGCGGGACG

ACGTGATCATCCCACAGCGTGCCATCCAGATGCTGTATGAGGAGACAAAC

GGCGAGGCCATCATCAGCACCGGCGTGGGCCAGCACCAGATGTGGGCGGC

GCAGTGGTACCAGTACAACGAGCCGCGGAGATGGGTCACGTCCGGCGGCC

TCGGTACGACGGCACTCCATGGGCTTTGGCCTGCCATCCGCCCTCGGCGC

GGCGGTGGCCCGGACGGTCGGCCCAAGAAGGTGGTGGTGGACATCGACGG

TTCCTGATGAACTGCCAGGAGCTGGCGACGGCGGCGGTGGAGGCGACGGC

AGTGCCTGGAGACCAAGATCATGATCCTCAACAACCAGCACCTGGGCATG

GTGGTCCAGTGGGAGGACCGCTTCTACAAGGCCAACCGCGCACACACCTA

CCTCGGCCACCGGGCCAATGAGTACCACACGACGCTGGACGAGAGCCACA

TCTTCCCCGACTTTGTCATGATGGCCAAGTCGTGCGGCGTCCCAGGCCGG

CGCGTCATCAAGCCCGAGGAGCTGCGCGGGGCCATCAGGGAGATGCTGGA

CACGCCCGGCCCCTTCCTGCTGGACGTGATGGTGCCGCATGTGGAGCACG

TGCTGCCCATGATCCCGGGCGGCGGCTCCTTCAAGGACATCATCACCAAG

GGCGACGGCCGCGACGAGTACTAA
```

In another embodiment, the isolated polynucleotide comprises a DNA sequence that is at least 60%, at least 70%, at least 80%, at least 85%, at least 90%, at least 95% or at least 98% homologous to the amino acid sequence of SEQ ID NO: 3. Each possibility represents a separate possibility of the invention.

In another embodiment, the isolated polynucleotide comprises a DNA sequence that is at least 60%, at least 70%, at least 80%, at least 85%, at least 90%, at least 95% or at least 98% identical to the amino acid sequence of SEQ ID NO: 3. Each possibility represents a separate possibility of the invention.

In another embodiment, the present invention comprises a AHAS or a nucleic acid encoding same combined with additional proteins and/or enzymes and/or substrates that are involved in the biosynthesis of BCCA. In another embodiment, the present invention comprises a composition comprising a AHAS or a nucleic acid molecule encoding same combined with additional proteins and/or enzymes and/or substrates that are involved in the biosynthesis of BCCA. In another embodiment, the present invention comprises a transformed or transfected cell comprising AHAS or a nucleic acid molecule encoding same combined with additional proteins and/or enzymes and/or substrates that are involved in the biosynthesis of BCCA. In another embodiment, the present invention comprises a transgenic alga comprising AHAS or a nucleic acid molecule encoding same combined with additional proteins and/or enzymes and/or substrates that are involved in the biosynthesis of BCCA.

In another embodiment, the present invention provides an algal AHAS or a nucleic acid molecule encoding same combined with additional algal proteins and/or enzymes and/or substrates that are involved in the biosynthesis of BCCA. In another embodiment, the alga is microalgae. In another embodiment, the present invention provides a microalgae AHAS or a nucleic acid molecule encoding same combined with additional microalgae proteins and/or enzymes and/or substrates that are involved in the biosynthesis of BCCA. In another embodiment, the microalgae is *Parietochloris incisa*. In another embodiment, the present invention provides a *Parietochloris incisa* AHAS or a nucleic acid molecule encoding same combined with additional *Parietochloris incisa* proteins and/or enzymes and/or substrates that are involved in the biosynthesis of BCCA.

In another embodiment, the present invention provides a combination of AHAS and additional proteins and/or enzymes and/or substrates involved in the biosynthesis of BCCA. In another embodiment, the present invention provides a combination of AHAS and Threonine deaminase (TD), ketol-acid Reductoisomerase (KARI), dihydroxyacid dehydratase (DHAD); transaminase (TA), 2-isopropylmalate synthase (2-IPMS), 3-isopropylmalate dehydratase (3-IPMD) and 3-isopropylmalate dehydrogenase (3-IPMDH). Each possibility represents a separate embodiment of the invention.

In another embodiment, the present invention provides a composition comprising the protein as described herein to be used in foodstuffs, dietary supplements or pharmaceutical compositions. In another embodiment, the present invention provides a composition comprising the protein described herein to be used in industrial applications for the manufacturing of BCCA. In another embodiment, the present invention provides composition comprising the BCCA. In another embodiment, a composition comprising BCCA is used in foodstuffs, dietary supplements or pharmaceutical compositions.

In another embodiment, an algal AHAS gene and AHAS protein of the present invention is superior when compared to its homologues with respect to efficient production of BCCA. In another embodiment, transforming a first alga with an algal AHAS derived from a second alga such as described herein is more efficient in the production of BCCA in comparison to transforming with a fungal AHAS. In another embodiment, transforming a first alga with an algal AHAS gene derived from a second alga such as described herein in combination with additional genes that encode proteins and/or enzymes involved in the biosynthesis of BCCA, is more efficient in the production of BCCA in comparison to transforming with AHAS fungal genes in combination with additional fungal genes. In another embodiment, the first alga is *P. incisa*. In another embodiment, *P. incisa* is the second alga. In another embodiment, *P. incisa* is the source of the additional genes that are involved in the biosynthesis of BCCA. In another embodiment, the source of the additional genes that are involved in the biosynthesis of BCCA is any organism comprising such genes.

In another embodiment, the present invention provides a method for producing branched-chain amino acid (BCCA) in a cell, comprising the step of transforming the cell with the polynucleotide as described herein. In another embodiment, the present invention provides a method for substantially enhancing the production of BCCA in a cell, comprising the step of transforming a cell with said polynucleotide as described herein.

In another embodiment, the present invention provides a method for producing branched-chain amino acid (BCCA) in a cell, comprising the step of transforming the cell with the polynucleotide as described herein, with an exogenous polynucleotide as described herein, with a combination of exogenous polynucleotides as described herein or with a vector comprising an exogenous polynucleotide as described herein, with a vector comprising a combination of exogenous polynucleotides as described herein, thereby producing BCCA in a cell, wherein each possibility represents a separate embodiment of the invention.

In another aspect, the present invention provides a protein comprising an amino acid sequence set forth in SEQ ID NO: 2. In one embodiment the present invention provides that the protein is a polypeptide. In another embodiment, the present invention provides that the protein is an enzyme. In another embodiment, the present invention provides a protein comprising an amino acid sequence set forth in SEQ ID NO: 1, wherein said sequence comprises at least one amino acid substitution. In another embodiment, the at least one amino acid substitution is at residue Trp 605. In another embodiment, the at least one amino acid substitution is W605S.

In another embodiment, the present invention provides a protein comprising the amino acid sequence:

(SEQ ID NO: 2)

MQGTMRPTAGALQQTVGCWHVPAGIPHAQQALRGRILPEELKQRCSATKP

RAARQSAVTAAKLAEGKAGTPSRSLRQQPAAPQQQQQQDSNELVALREA

AKASLSSPAPAEWVDRFGSEPRKGADILVQCLEREGAFRVFAYPGGASME

IHQALTRSGIIRNILCRHEQGEIFAAEGYAKCTGDVGVCIATSGPGATNL

VTGLADAMLDSVPLVAITGQVPRKMIGTDGFQETPIVEVTRQITKHNFLV

MDLDDLPRIMKEAFYLARTGRPGPVLVDVPKDIQQQLAVPDWDTPMAISG

YMSRLPAPPNPSQLAAVVRALKEAKRPTLYVGGGALDSSAELREFVRLTG

IPVAQTLMGLGTFPEEDPLALQMLGMHGTVYANYAVNDSDLLLAFGVRFD

DRVTGKLEAFASRACIVHIDIDPAEICKNKEAHIPICADLRASLIALNEL

LRRDPLPEGAFADWRAAIEAKKQEFPMTFPERDDVIIPQRAIQMLYEETN

GEAIISTGVGQHQMWAAQWYQYNEPRRWVTSGGLGSMGFGLPSALGAAAV

AYDGTDGRPKKVVVDIDGDGSFLMNCQELATAAVEGLETKIMILNNQHLG

MVVQSEDRFYKANRAHTYLGHRANEYHTTLDESHIFPDFVMMAKSCGVPG

RRVIKPEELRGAIREMLDTPGPFLLDVMVPHVEHVLPMIPGGGSFKDIIT

KGDGRDEY.

In another embodiment, the protein comprises an amino acid sequence that is at least 60%, at least 70%, at least 80%, at least 85%, at least 90%, at least 95% or at least 98% homologous to the amino acid sequence of SEQ ID NO: 2. Each possibility represents a separate possibility of the invention.

In another embodiment, the protein comprises an amino acid sequence that is at least 60%, at least 70%, at least 80%, at least 85%, at least 90%, at least 95% or at least 98% identical to the amino acid sequence of SEQ ID NO: 2. Each possibility represents a separate possibility of the invention.

In another embodiment, the protein as described herein, comprises at least a portion of the amino acid shown in SEQ ID NO: 2. In another embodiment, the protein as described herein is a variant of SEQ ID NO: 2.

In another embodiment, the present invention provides a polynucleotide encoding a protein comprising the amino acid set forth in SEQ ID NO: 2. In another embodiment, the polynucleotide is a DNA molecule. In another embodiment, the polynucleotide is a cDNA molecule.

In another embodiment, the polynucleotide comprises a DNA sequence comprising the sequence:

(SEQ ID NO: 4)

ATGCAAGGCACTATGCGGCCGACGGCTGGAGCACTGCAGCAGACCGTCGG

CTGCTGGCACGTCCCGGCCGGCATCCCCCACGCACAGCAGGCGCTGCGAG

GCCGTATACTGCCCGAGGAGCTGAAGCAGCGGTGTTCAGCAACCAAACCT

AGGGCGGCCAGGCAGTCAGCGGTGACCGCTGCCAAGCTTGCAGAGGGCAA

GGCAGGCACACCATCACGGAGCTTGCGGCAGCAGCCGGCAGCGCCGCAGC

AGCAGCAGCAGCAGCAGGATAGCAATGAGCTGGTGGCGTTGCGGGAGGCT

GCCAAGGCCTCGCTCTCATCCCCCGCGCCAGCCGAGTGGGTGGATCGGTT

TGGGTCGGAGCCCCGCAAGGGCGCGGATATCCTGGTGCAGTGCCTGGAGC

GCGAGGGGGCCTTCCGCGTGTTTGCCTACCCCGGCGGCGCCAGCATGGAG

ATCCATCAGGCCTTGACGCGCAGCGGCATCATCCGCAACATCCTGTGCCG

CCATGAGCAGGGCGAGATCTTTGCGGCGGAGGGCTATGCCAAGTGCACGG

GCGATGTGGGCGTGTGCATCGCGACCAGCGGGCCCGGCGCCACCAACCTC

GTGACTGGCCTGGCTGATGCCATGCTGGACAGCGTTCCGCTTGTTGCCAT

CACAGGGCAGGTGCCCCGCAAGATGATCGGCACGGACGGGTTCCAGGAGA

CGCCGATTGTGGAGGTGACGCGGCAGATCACCAAGCACAACTTCCTGGTC

ATGGACCTGGATGACCTGCCGCGCATCATGAAGGAGGCATTCTACCTGGC

GCGCACGGGGCGGCCGGGCCCGGTGCTGGTGGATGTGCCCAAGGACATCC

AGCAGCAGCTGGCGGTGCCGGACTGGGACACGCCCATGGCCATCAGCGGC

TACATGTCGCGCCTGCCGGCCCCGCCTAACCCCTCACAGCTGGCCGCGGT

CGTGCGCGCGCTGAAGGAGGCTAAGAGGCCGACGCTGTACGTGGGCGGTG

GCGCGCTCGACTCGAGCGCTGAGCTGCGCGAGTTTGTGCGGCTGACGGGC

ATCCCCGTCGCGCAGACGCTTATGGGCCTGGGCACCTTCCCCGAGGAAGA

CCCGCTGGCACTGCAGATGCTGGGCATGCACGGTACGGTGTACGCCAACT

ACGCCGTCAACGACAGCGACCTGCTGCTGGCGTTTGGCGTGCGCTTCGAC

GACCGCGTGACTGGCAAGCTGGAGGCGTTTGCTTCGCGCGCGTGCATCGT

GCACATCGACATCGACCCTGCGGAGATCTGCAAGAACAAGGAGGCCCACA

TACCCATCTGTGCAGACCTGCGTGCGTCGTTGATAGCGCTGAATGAGCTG

TTGCGGCGAGACCCTCTGCCAGAGGGCGCCTTTGCGGACTGGCGGGCGGC

CATTGAGGCCAAGAAGCAGGAGTTCCCCATGACCTTCCCGGAGCGGGACG

ACGTGATCATCCCACAGCGTGCCATCCAGATGCTGTATGAGGAGACAAAC

GGCGAGGCCATCATCAGCACCGGCGTGGGCCAGCACCAGATGTGGGCGGC

GCAGTGGTACCAGTACAACGAGCCGCGGAGATGGGTCACGTCCGGCGGCC

TCGGCTCCATGGGCTTTGGCCTGCCATCCGCCCTCGGCGCGGCGGTGGCC

TACGACGGCACGGACGGTCGGCCCAAGAAGGTGGTGGTGGACATCGACGG

CGACGGCAGTTTCCTGATGAACTGCCAGGAGCTGGCGACGGCGGCGGTGG

AGGGCCTGGAGACCAAGATCATGATCCTCAACAACCAGCACCTGGGCATG

GTGGTCCAGTCGGAGGACCGCTTCTACAAGGCCAACCGCGCACACACCTA

CCTCGGCCACCGGGCCAATGAGTACCACACGACGCTGGACGAGAGCCACA

TCTTCCCCGACTTTGTCATGATGGCCAAGTCGTGCGGCGTCCCAGGCCGG

CGCGTCATCAAGCCCGAGGAGCTGCGCGGGGCCATCAGGGAGATGCTGGA

-continued

```
CACGCCCGGCCCCTTCCTGCTGGACGTGATGGTGCCGCATGTGGAGCACG

TGCTGCCCATGATCCCGGGCGGCGGCTCCTTCAAGGACATCATCACCAAG

GGCGACGGCCGCGACGAGTACTAA
```

In another embodiment, the polynucleotide comprises a DNA sequence that is at least 60%, at least 70%, at least 80%, at least 85%, at least 90%, at least 95% or at least 98% homologous to the amino acid sequence of SEQ ID NO: 4. Each possibility represents a separate possibility of the invention.

In another embodiment, the polynucleotide comprises a DNA sequence that is at least 60%, at least 70%, at least 80%, at least 85%, at least 90%, at least 95% or at least 98% identical to the amino acid sequence of SEQ ID NO: 4. Each possibility represents a separate possibility of the invention.

In another embodiment, the present invention comprises a composition comprising a protein comprising or consisting the sequence set forth in SEQ ID NO: 2 or a nucleic acid molecule encoding same. In another embodiment, the present invention comprises a transformed or transfected cell comprising the protein comprising the sequence set forth in SEQ ID NO: 2 or a nucleic acid molecule encoding same. In another embodiment, the present invention comprises a transgenic alga comprising the protein comprising the sequence set forth in SEQ ID NO: 2 or a nucleic acid molecule encoding same.

In another embodiment, the present invention provides a protein isolated from alga and further mutated, the protein comprising the sequence set forth in SEQ ID NO: 2 or a nucleic acid molecule encoding same. In another embodiment, the alga is microalgae. In another embodiment, the present invention provides a protein isolated from microalgae and further mutated, the protein comprising the sequence set forth in SEQ ID NO: 2 or a nucleic acid molecule encoding same. In another embodiment, the microalgae is *Parietochloris incisa*. In another embodiment, the present invention provides a protein isolated from *Parietochloris incisa* and further mutated, the protein comprising the sequence set forth in SEQ ID NO: 2 or a nucleic acid molecule encoding same.

In another embodiment, the present invention provides a combination of the protein comprising the sequence set forth in SEQ ID NO: 2 and additional proteins conferring resistance to herbicides. In another embodiment, the present invention provides a combination of the protein comprising the sequence set forth in SEQ ID NO: 2 and proteins having target-site mutations which confer resistance to herbicides. In another embodiment, proteins having target-site mutations which confer resistance to herbicides include but are not limited to phytoene desaturase (PDS) and tubulin.

In another embodiment, the present invention provides a method for conferring herbicide resistance in a cell comprising the step of transforming the cell with a polynucleotide encoding the protein comprising the sequence set forth in SEQ ID NO: 2. In another embodiment, the present invention provides a method for conferring herbicide resistance in a cell comprising the step of transforming the cell with a polynucleotide comprising the sequence set forth in SEQ ID NO: 4.

In another embodiment, the present invention provides a method for conferring resistance to herbicides in a cell, comprising the step of transforming the cell with a polynucleotide comprising the sequence set forth in SEQ ID NO: 4, wherein the herbicides include but are not limited to sulfonylureas, imidazolinones and triazolopyrimidines. In another embodiment, sulfonylurea herbicides include but are not limited to pyrimidinylsulfonylurea herbicides and triazinylsulfonylurea herbicides. In another embodiment, pyrimidinylsulfonylurea herbicides include but are not limited to: amidosulfuron, azimsulfuron, bensulfuron, chlorimuron, cyclosulfamuron, ethoxysulfuron, flazasulfuron, flucetosulfuron, flupyrsulfuron, foramsulfuron, halo sulfuron, imazosulfuron, me s o sulfuron, metazosulfuron, methiopyrisulfuron, monosulfuron, nicosulfuron, orthosulfamuron, oxasulfuron, primisulfuron propyrisulfuron, pyrazosulfuron, rimsulfuron, sulfometuron, sulfometuron methyl, sulfosulfuron, trifloxysulfuron and zuomihuanglong. In another embodiment, triazinylsulfonylurea herbicides include but are not limited to chlorsulfuron, cinosulfuron, ethametsulfuron, iodosulfuron, iofensulfuron, metsulfuron, prosulfuron, thifensulfuron, triasulfuron, tribenuron, triflusulfuron and tritosulfuron.

In another embodiment, the present invention provides a method for conferring herbicide resistance in a cell, comprising the step of transforming the cell with the polynucleotide described herein, wherein the cell produces long-chain polyunsaturated fatty acid (LC-PUFA), arachidonic acid (ARA) and rich triacylglycerols (TAG). In another embodiment, the present invention provides a method for conferring herbicide resistance in an alga, comprising the step of transforming the alga with the polynucleotide described herein, wherein the alga produces long-chain polyunsaturated fatty acid (LC-PUFA), arachidonic acid (ARA) and rich triacylglycerols (TAG). In another embodiment, the present invention provides a method for conferring herbicide resistance in *Parietochloris incisa*, comprising the step of transforming e *Parietochloris incisa* with the polynucleotide described herein, wherein *Parietochloris incisa* produces long-chain polyunsaturated fatty acid (LC-PUFA), arachidonic acid (ARA) and rich triacylglycerols (TAG).

In another embodiment, the method of the present invention further comprises the step of transforming a cell with at least one polynucleotide encoding an enzyme involved in the biosynthesis of ω-3 LC-PUFA, thereby producing a cell having herbicide resistance and at least one enzyme involved in the biosynthesis of ω-3 LC-PUFA. In another embodiment, the method of the present invention further comprises the step of transforming a cell with ω-3 desaturase, C20 PUFA elongase, Δ4 desaturase or combinations thereof, thereby producing a cell having herbicide resistance and at least one enzyme involved in the biosynthesis of ω-3 LC-PUFA.

In another embodiment, the expression and/or transcription of the enzyme involved in the biosynthesis of ω-3 LC-PUFA as described herein is up-regulated during nitrogen starvation. In another embodiment, the expression and/or transcription of ω-3 desaturase, C20 PUFA elongase and Δ4 desaturase as described herein, is up-regulated during nitrogen starvation.

In another embodiment, the protein comprising the sequence set forth in SEQ ID NO: 2 is used indirectly or directly for conferring herbicide resistance in cells and capable of producing polyunsaturated fatty acids. In another embodiment, "Directly" is meant to encompass the situation where the enzyme directly enhances herbicide resistance in a cell. In another embodiment, "Indirectly" is meant to encompass the situation where a protein, other than the protein of the invention, is modified to be herbicide resistant by the protein of the invention, described herein. In another embodiment, a very long-chain polyunsaturated fatty acid produced by cells having herbicide resistance, either directly or indirectly is added to a nutritional composition, pharmaceutical compositions, cosmetics, and animal feeds, all of which are encompassed by the present invention.

In another embodiment, a long-chain polyunsaturated fatty acid produced by a protein or a combination of proteins in a cell or alga cell having herbicide resistance produced by methods described herein, is utilized in an infant formula. In another embodiment, a long-chain polyunsaturated fatty acid produced by a protein or a combination of proteins in a cell or alga cell having herbicide resistance produced by methods described herein, is administered to a subject having a deficiency in very long-chain polyunsaturated fatty acid.

In another embodiment, a cell is a eukaryotic cell. In another embodiment, a cell is a prokaryotic cell. In another embodiment, a cell is a plant cell. In another embodiment, a cell is an algal cell. In another embodiment, a cell is a microalga cell. In another embodiment, a cell is a *Parietochloris incisa* cell. In another embodiment, a cell is a transfected cell. In another embodiment, a cell is transiently transfected with a polynucleotide or a combination of polynucleotides as described herein. In another embodiment, a cell is stably transfected cell with a polynucleotide or a combination of polynucleotides as described herein.

In another embodiment, the present invention provides a composition comprising a polypeptide as described herein. In another embodiment, the present invention provides a composition comprising a polypeptide comprising an amino acid sequence set forth in SEQ ID NO: 1 or SEQ ID NO: 2. Each possibility represents a separate embodiment of the invention.

In another embodiment, the present invention provides a composition comprising the polynucleotide as described herein. In another embodiment, the present invention provides a composition comprising the polynucleotide encoding the protein comprising the amino acid sequence set forth in SEQ ID NO: 1 or SEQ ID NO: 2. Each possibility represents a separate embodiment of the invention.

In another embodiment, the present invention provides a composition comprising the polynucleotide comprising the sequence set forth in SEQ ID NO: 3 or SEQ ID NO: 4. Each possibility represents a separate embodiment of the invention.

In another embodiment, the present invention provides a composition comprising a vector comprising a polynucleotide as described herein. In another embodiment, the present invention provides composition comprising a combination of vectors which comprise polynucleotides as described herein. In another embodiment, a composition such as described herein, comprises an excipient. In another embodiment, a composition such as described herein, comprises a carrier. In another embodiment, a carrier stabilizes a protein or a nucleic acid molecule of the invention. In another embodiment, one of skill in the art will readily identify a known suitable carrier to be used with the composition as described herein. In another embodiment, one of skill in the art is able to prepare a composition comprising AHAS as described herein, or a polynucleotide as described herein, or a combination of polynucleotides and vectors as described herein. Each possibility represents a separate embodiment of the invention.

In another embodiment, algae as described herein are eukaryotic organisms. In another embodiment, algae as described herein are photoautotrophic. In another embodiment, algae as described herein are mixotrophic. In another embodiment, algae as described herein are unicellular. In another embodiment, algae as described herein are multicellular. In another embodiment, algae as described herein are Excavata algae. In another embodiment, algae as described herein are Rhizaria algae. In another embodiment, algae as described herein are Chromista algae. In another embodiment, algae as described herein are Alveolata algae.

Polypeptides and Polynucleotides

In some embodiments, the terms "protein" or "polypeptide" are used herein interchangeably and encompasses native polypeptides (either degradation products, synthetically synthesized polypeptides or recombinant polypeptides) and peptidomimetics (typically, synthetically synthesized polypeptides), as well as peptoids and semipeptoids which are polypeptide analogs, which have, in some embodiments, modifications rendering the polypeptides/proteins even more stable while in a body or more capable of penetrating into cells.

In some embodiments, modifications include, but are not limited to N terminus modification, C terminus modification, polypeptide bond modification, including, but not limited to, CH2-NH, CH2-S, CH2-S═O, O═C—NH, CH2-O, CH2-CH2, S═C—NH, CH═CH or CF═CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein.

In some embodiments, polypeptide bonds (—CO—NH—) within the polypeptide are substituted. In some embodiments, the polypeptide bonds are substituted by N-methylated bonds (—N(CH3)—CO—), by ester bonds (—C(R)H—C—O—O—C(R)—N—), by ketomethylene bonds (—CO—CH2-) or α-aza bonds (—NH—N(R)—CO—), wherein R is any alkyl, e.g., methyl, carbo bonds (—CH2-NH—). Each possibility represents a separate embodiment of the invention. In some embodiments, the polypeptide bonds are substituted by hydroxyethylene bonds (—CH(OH)—CH2-), by thioamide bonds (—CS—NH—), by olefinic double bonds (—CH═CH—) or by retro amide bonds (—NH—CO—), by polypeptide derivatives (—N(R)—CH2-CO—), wherein R is the "normal" side chain, naturally presented on the carbon atom. In some embodiments, these modifications occur at any of the bonds along the polypeptide chain and even at several (2-3 bonds) at the same time.

In some embodiments, natural aromatic amino acids of the polypeptide such as Trp, Tyr and Phe, be substituted for synthetic non-natural acid such as Phenylglycine, TIC, naphthylelanine (Nol), ring-methylated derivatives of Phe, halogenated derivatives of Phe or o-methyl-Tyr. In some embodiments, the polypeptides of the present invention include one or more modified amino acid or one or more non-amino acid monomers (e.g., fatty acid, complex carbohydrates, etc.).

In one embodiment, "amino acid" or "amino acids" is understood to include the 20 naturally occurring amino acid; those amino acid often modified post-translationally in vivo, including, for example, hydroxyproline, phosphoserine and phosphothreonine; and other unusual amino acid including, but not limited to, 2-aminoadipic acid, hydroxylysine, isodesmosine, nor-valine, nor-leucine and ornithine. In one embodiment, "amino acid" includes both D- and L-amino acid.

In some embodiments, the polypeptides or proteins of the present invention are utilized in a soluble form. In some embodiments, the polypeptides or proteins of the present invention include one or more non-natural or natural polar amino acid, including but not limited to serine and threonine which are capable of increasing polypeptide or protein solubility due to their hydroxyl-containing side chain.

In some embodiments, the polypeptides or proteins of the present invention are utilized in a linear form, although it will be appreciated by one skilled in the art that in cases where cyclization does not severely interfere with polypeptide characteristics, cyclic forms of the polypeptide can also be utilized.

In some embodiments, the polypeptides or proteins of present invention are biochemically synthesized such as by using standard solid phase techniques. In some embodiments, these biochemical methods include exclusive solid phase synthesis, partial solid phase synthesis, fragment condensation, or classical solution synthesis. In some embodiments, these methods are used when the polypeptide is relatively short (about 5-15 kDa) and/or when it cannot be produced by recombinant techniques (i.e., not encoded by a nucleic acid sequence) and therefore involves different chemistry.

In some embodiments, solid phase polypeptide or protein synthesis procedures are well known to one skilled in the art and further described by John Morrow Stewart and Janis Dillaha Young, Solid Phase Polypeptide Syntheses (2nd Ed., Pierce Chemical Company, 1984). In some embodiments, synthetic polypeptides or proteins are purified by preparative high performance liquid chromatography [Creighton T. (1983) Proteins, structures and molecular principles. WH Freeman and Co. N.Y.], and the composition of which can be confirmed via amino acid sequencing by methods known to one skilled in the art.

In some embodiments, recombinant protein techniques are used to generate the polypeptides of the present invention. In some embodiments, recombinant protein techniques are used for generation of relatively long polypeptides (e.g., longer than 18-25 amino acid). In some embodiments, recombinant protein techniques are used for the generation of large amounts of the polypeptide of the present invention. In some embodiments, recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al, (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

In one embodiment, a polypeptide or protein of the present invention is synthesized using a polynucleotide encoding a polypeptide or protein of the present invention. In some embodiments, the polynucleotide encoding a polypeptide of the present invention is ligated into an expression vector, comprising a transcriptional control of a cis-regulatory sequence (e.g., promoter sequence). In some embodiments, the cis-regulatory sequence is suitable for directing constitutive expression of the polypeptide of the present invention. In some embodiments, the cis-regulatory sequence is suitable for directing tissue specific expression of the polypeptide of the present invention. In some embodiments, the cis-regulatory sequence is suitable for directing inducible expression of the polypeptide of the present invention.

In one embodiment, the phrase "a polynucleotide" refers to a single or double stranded nucleic acid sequence which may be isolated and provided in the form of an RNA sequence, a complementary polynucleotide sequence (cDNA), a genomic polynucleotide sequence and/or a composite polynucleotide sequences (e.g., a combination of the above). Each possibility represents a separate embodiment of the invention. In one embodiment, "genomic polynucleotide sequence" refers to a sequence derived (isolated) from a chromosome and thus it represents a contiguous portion of a chromosome.

In one embodiment, "composite polynucleotide sequence" refers to a sequence, which is at least partially complementary and at least partially genomic. In one embodiment, a composite sequence can include some exonal sequences required to encode the polypeptide of the present invention, as well as some intronic sequences interposing there between. In one embodiment, the intronic sequences can be of any source, including of other genes, and typically will include conserved splicing signal sequences. In one embodiment, intronic sequences include cis acting expression regulatory elements.

In one embodiment, the polynucleotides of the present invention further comprise a signal sequence encoding a signal peptide for the secretion of the polypeptides of the present invention. In one embodiment, following expression, the signal peptides are cleaved from the precursor proteins resulting in the mature proteins.

In some embodiments, polynucleotides of the present invention are prepared using PCR techniques or any other method or procedure known to one skilled in the art. In some embodiments, the procedure involves the legation of two different DNA sequences (See, for example, "Current Protocols in Molecular Biology", eds. Ausubel et al., John Wiley & Sons, 1992).

In one embodiment, polypeptides or proteins of the present invention are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, the polypeptide or protein of the present invention is retrieved in "substantially pure" form. In one embodiment, the phrase "substantially pure" refers to a purity that allows for the effective use of the protein in the applications described herein.

In one embodiment, the polypeptide or protein of the present invention can also be synthesized using in vitro expression systems. In one embodiment, in vitro synthesis methods are well known in the art and the components of the system are commercially available.

Expression and Transformation Systems

In another embodiment, the terms "transformation", "transduction", "transfection" and "conjugation" are used herein interchangeably and refer to the insertion of new genetic material into nonbacterial cells including animal and plant cells, applied to eukaryotic and prokaryotic cells.

In another embodiment, the present invention provides an engineered organism such as a transgenic plant, a transgenic seed, a transgenic alga and a transgenic animal. Each possibility represents a separate embodiment of the invention. In another embodiment, an engineered organism is engineered to express a protein, a polypeptide, a combination of polypeptides, a polynucleotide and a combination of polynucleotides as described herein. Each possibility represents a separate embodiment of the invention.

In one embodiment, polynucleotides of the present invention are inserted into expression vectors (i.e., a nucleic acid construct) to enable expression of the recombinant polypeptide. In one embodiment, the expression vector of the present invention includes additional sequences which render this vector suitable for replication and integration in prokaryotes. In one embodiment, the expression vector of the present invention includes additional sequences which render this vector suitable for replication and integration in eukaryotes. In one embodiment, the expression vector of the present invention includes a shuttle vector which renders this vector suitable for replication and integration in both prokaryotes and eukaryotes. In some embodiments, cloning vectors comprise transcription and translation initiation sequences (e.g., promoters, enhancers) and transcription and translation terminators (e.g., polyadenylation signals).

In one embodiment, a variety of prokaryotic or eukaryotic cells can be used as host-expression systems to express the polypeptides of the present invention. In some embodiments, these include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

In some embodiments, non-bacterial expression systems are used (e.g., plant expression systems) to express the polypeptide of the present invention. In one embodiment, yeast expression systems are used. In one embodiment, algae expression systems are used. In one embodiment, plant expression systems are used. In one embodiment, a number of vectors containing constitutive or inducible promoters can be used in yeast as disclosed in U.S. Pat. No: 5,932,447 which is hereby incorporated in its entirety by reference. In another embodiment, vectors which promote integration of foreign DNA sequences into the yeast chromosome are used.

In another embodiment, expression in a host cell can be accomplished in a transient or a stable fashion. In another embodiment, a host cell is a cell as described herein. In another embodiment, transient expression is from introduced constructs which contain expression signals functional in the host cell, but which constructs do not replicate and rarely integrate in the host cell, or where the host cell is not proliferating. In another embodiment, transient expression also can be accomplished by inducing the activity of a regulatable promoter operably linked to the gene of interest.

In another embodiment, stable expression is achieved by introduction of a construct that integrates into the host genome. In another embodiment, stable expression comprises autonomously replication within the host cell. In another embodiment, stable expression of the polynucleotide of the invention is selected for the use of a selectable marker located on or transfected with the expression construct, followed by selection for cells expressing the marker. In another embodiment, the site of the construct's integration can occur randomly within the host genome or can be targeted through constructs containing regions of homology with the host genome sufficient to target recombination with the host locus. In another embodiment, constructs are targeted to an endogenous locus, all or some of the transcriptional and translational regulatory regions can be provided by the endogenous locus.

In another embodiment, a plant or plant tissue is utilized as a host or host cell, respectively, for expression of the protein/s disclosed herein, used in turn, for the production of BCCA In another embodiment, a vector which comprises a DNA sequence encoding the protein/s as described herein is linked to a promoter, and is introduced into the plant tissue or plant for a time and under conditions sufficient for expression of the protein.

In another embodiment, the regeneration, development, and cultivation of plants from single plant protoplast transformants or from various transformed explants is well known in the art (for example: Weissbach and Weissbach, In: Methods for Plant Molecular Biology, (Eds.), Academic Press, Inc. San Diego, Calif., (1988)). In another embodiment, regeneration and growth process comprises the steps of selection of transformed cells, culturing those individualized cells through the usual stages of embryonic development through the rooted plantlet stage. In another embodiment, transgenic embryos and seeds are similarly regenerated. In another embodiment, resulting transgenic rooted shoots are thereafter planted in an appropriate plant growth medium such as soil.

In another embodiment, regeneration and growth process of algae are known to one of skill in the art. In another embodiment, identification, selection, of transgenic algae are known to one of skill in the art.

In another embodiment, development or regeneration of plants containing an exogenous polynucleotide as described herein encodes a protein as described herein and is well known in the art. In another embodiment, development or regeneration of algae containing an exogenous polynucleotide as described herein encodes a protein as described herein and is well known in the art. In another embodiment, the regenerated plants are self-pollinated to provide homozygous transgenic plants. In another embodiment, pollen obtained from the regenerated plants is crossed to seed-grown plants of agronomically important lines. In another embodiment, pollen from plants of these important lines is used to pollinate regenerated plants. In another embodiment, a transgenic plant of the present invention containing a desired polypeptide is cultivated using methods well known to one skilled in the art.

In another embodiment, a variety of methods can be utilized for the regeneration of plants from plant tissue. In another embodiment, the method of regeneration will depend on the starting plant tissue and the particular plant species to be regenerated. In another embodiment, methods for transforming dicots, primarily by use of *Agrobacterium tumefaciens*, and obtaining transgenic plants are known in the art McCabe et al., Biol. Technology 6:923 (1988), Christou et al., Plant Physiol. 87:671-674 (1988)); Cheng et al., Plant Cell Rep. 15:653657 (1996), McKently et al., Plant Cell Rep. 14:699-703 (1995)); Grant et al., Plant Cell Rep. 15:254-258, (1995).

In another embodiment, transformation of monocotyledons using electroporation, particle bombardment, and *Agrobacterium* are known in the art. In another embodiment, transformation and plant regeneration are well established in the art. In another embodiment, assays for gene expression based on the transient expression of cloned nucleic acid constructs have been developed by introducing the nucleic acid molecules into plant cells by polyethylene glycol treatment, electroporation, or particle bombardment (Marcotte et al., Nature 335:454-457 (1988); Marcotte et al., Plant Cell 1:523-532 (1989); McCarty et al., Cell 66:895-905 (1991); Hattori et al., Genes Dev. 6:609-618 (1992); Goff et al., EMBO J. 9:2517-2522 (1990)).

In another embodiment, transient expression systems are used to functionally dissect the oligonucleotides constructs. In another embodiment, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., Molecular Cloning: A Laboratory Manual, Cold Spring Harbor Press (1989); Maliga et al., Methods in Plant Molecular Biology, Cold Spring Harbor Press (1995); Birren et al., Genome Analysis: Detecting Genes, 1, Cold Spring Harbor, N.Y. (1998); Birren et al., Genome Analysis: Analyzing DNA, 2, Cold Spring Harbor, N.Y. (1998); Plant Molecular Biology: A Laboratory Manual, eds. Clark, Springer, N.Y. (1997)).

In one embodiment, the expression vector of the present invention can further include additional polynucleotide sequences that allow, for example, the translation of several proteins from a single mRNA such as an internal ribosome entry site (IRES) and sequences for genomic integration of the promoter-chimeric polypeptide.

In some embodiments, expression vectors containing regulatory elements from eukaryotic viruses such as retroviruses are used by the present invention. In some embodiments, recombinant viral vectors are useful for in vivo expression of the polypeptides of the present invention since they offer advantages such as lateral infection and targeting specificity. In one embodiment, lateral infection is inherent in the life cycle of, for example, retrovirus, and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide or protein), the expression construct of the present invention can also include sequences engineered to optimize stability, production, purification, yield or activity of the expressed polypeptide or protein.

In some embodiments, transformed cells are cultured under effective conditions, which allow for the expression of high amounts of recombinant polypeptide or protein. In some embodiments, effective culture conditions include, but are not limited to, effective media, bioreactor, temperature, pH and oxygen conditions that permit protein production. In one embodiment, an effective medium refers to any medium in which a cell is cultured to produce the recombinant polypeptide or protein of the present invention. In some embodiments, a medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

In some embodiments, depending on the vector and host system used for production, resultant polypeptides or proteins of the present invention either remain within the recombinant cell, secreted into the fermentation medium, secreted into a space between two cellular membranes, or retained on the outer surface of a cell or viral membrane.

Nutritional Compositions

In another embodiment, the described compositions are utilized in connection with animals (i.e., domestic or non-domestic), as well as humans, as animals experience many of the same needs and conditions as humans.

In another embodiment, nutritional compositions include any food or preparation for human or animal consumption including for enteral or parenteral consumption, which when taken into the body (a) serve to nourish or build up tissues or supply energy and/or (b) maintain, restore or support adequate nutritional status or metabolic functions. In another embodiment, the composition includes edible macronutrients, vitamins and minerals in amounts desired for a particular use. In another embodiment, the amount of such ingredients will vary depending on whether the composition is intended for use with normal, healthy infants, children or adults having specialized needs such as those which accompany certain metabolic conditions (e.g., metabolic disorders).

In another embodiment, the macronutrients include edible fats, carbohydrates and proteins. In another embodiment, edible fats include but are not limited to coconut oil, soy oil, and mono- and diglycerides. In another embodiment, carbohydrates include but are not limited to glucose, edible lactose and hydrolyzed search. In another embodiment, proteins which are utilized in the nutritional composition of the invention include but are not limited to soy proteins, electrodialysed whey, electrodialysed skim milk, milk whey, or the hydrolysates of these proteins.

In another embodiment, vitamins and minerals are added to the nutritional compositions of the present invention and include but are not limited to: calcium, phosphorus, potassium, sodium, chloride, magnesium, manganese, iron, copper, zinc, selenium, iodine, and Vitamins A, E, D, C, and the B complex. Other such vitamins and minerals may also be added.

In another embodiment, components utilized in the nutritional compositions of the present invention will be of semi-purified or purified origin. By semi-purified or purified is meant a material which has been prepared by purification of a natural material or by synthesis. In another embodiment, nutritional compositions of the present invention include but are not limited to infant formulas, dietary supplements, dietary substitutes, and rehydration compositions. In another embodiment, a nutritional composition of the present invention may also be added to food even when supplementation of the diet is not required. In another embodiment, a composition is added to food of any type including but not limited to margarines, modified butters, cheeses, milk, yogurt, chocolate, candy, snacks, salad oils, cooking oils, cooking fats, meats, fish and beverages.

In another embodiment, a nutritional composition is an enteral nutritional product. In another embodiment, a nutritional composition is an adult or pediatric enteral nutritional product. In another embodiment, a composition is administered to adults or children experiencing stress or having specialized needs due to chronic or acute disease states. In another embodiment, a composition comprises, in addition to polyunsaturated fatty acids produced in accordance with the present invention, macronutrients, vitamins and minerals as described above. In another embodiment, the macronutrients may be present in amounts equivalent to those present in human milk or on an energy basis, i.e., on a per calorie basis.

In another embodiment, the present invention includes an enteral formula comprising polyunsaturated fatty acids produced in accordance with the teachings of the present invention. In another embodiment, an enteral formula is sterilized and subsequently utilized on a ready-to-feed basis or stored in a concentrated liquid or powder. In another embodiment, a powder is prepared by spray drying the formula prepared as indicated above, and reconstituting it by rehydrating the concentrate. In another embodiment, the present invention includes an adult and pediatric nutritional formulas. In another embodiment, adult and pediatric nutritional formulas are known in the art and are commercially available (e.g., Similac®, Ensure®, Jevity® and Alimentum® from Ross Products Division, Abbott Laboratories).

In another embodiment, PUFAs produced in accordance with the present invention, or derivatives thereof, are added to a dietary substitute or supplement, particularly an infant formula, for patients undergoing intravenous feeding or for preventing or treating malnutrition or other conditions or disease states. In another embodiment, PUFAs produced in accordance with the present invention are used to alter, the composition of infant formulas in order to better replicate the PUFA content of human breast milk or to alter the presence of PUFAs normally found in a non-human mammal's milk.

Pharmaceutical Composition

In one embodiment, the polypeptides or proteins of the present invention can be provided to the individual as part of a pharmaceutical composition where it is mixed with a pharmaceutically acceptable carrier. In one embodiment, a "pharmaceutical composition" refers to a preparation of one or more of the active ingredients described herein with other chemical components such as physiologically suitable carriers and excipients. The purpose of a pharmaceutical composition is to facilitate administration of a compound to an organism. In one embodiment, "active ingredient" refers to the polypeptide or protein sequence of interest.

In one embodiment, the phrase "physiologically acceptable carrier" refers to a carrier or a diluent that does not cause significant irritation to a tissue such as a plant tissue or a cell such as a plant cell; and does not abrogate the biological activity and properties of the protein or polynucleotide of the invention. An adjuvant is included under these phrases. In one embodiment, one of the ingredients included in the physiologically acceptable carrier can be for example polyethylene glycol (PEG), a biocompatible polymer with a wide range of solubility in both organic and aqueous media (Mutter et al. (1979).

In one embodiment, "excipient" refers to an inert substance added to the composition to further facilitate administration of an active ingredient. In one embodiment, excipients include calcium carbonate, calcium phosphate, various sugars and types of starch, cellulose derivatives, gelatin, vegetable oils and polyethylene glycols.

In another embodiment, techniques for formulation and administration of peptide to plants or in-vitro are known to one of skill in the art. In one embodiment, compositions of the present invention are manufactured by processes well known in the art, e.g., by means of conventional mixing, dissolving, or lyophilizing processes. In one embodiment, compositions for use in accordance with the present invention is formulated in conventional manner using one or more physiologically acceptable carriers comprising excipients and auxiliaries, which facilitate processing of the proteins/polynucleotides into preparations. In one embodiment, formulation is dependent upon the method of administration chosen.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives. The compositions can be used as sprays, mists, drops, and the like.

Additionally, suspensions of the active ingredients, in some embodiments, are prepared as appropriate oily or water based suspensions. Suitable lipophilic solvents or vehicles include, in some embodiments, fatty oils such as sesame oil, or synthetic fatty acid esters such as ethyl oleate, triglycerides or liposomes. Aqueous injection suspensions contain, in some embodiments, substances, which increase the viscosity of the suspension, such as sodium carboxymethyl cellulose, sorbitol or dextran. In another embodiment, the suspension also contains suitable stabilizers or agents, which increase the solubility of the active ingredients to allow for the preparation of highly concentrated solutions.

In another embodiment, the proteins as described herein can be delivered in a vesicle, in particular a liposome (see Langer, *Science* 249:1527-1533 (1990); Treat et al., in Liposomes in the Therapy of Infectious Disease and Cancer, Lopez- Berestein and Fidler (eds.), Liss, New York, pp. 353-365 (1989); Lopez-Berestein, ibid., pp. 317-327; see generally ibid). In some embodiments, the protein as described herein is in powder form for constitution with a suitable vehicle, e.g., sterile, pyrogen-free water based solution, before use. In another embodiment, compositions are contained in a container with attached atomizing means.

In some embodiments, compositions suitable for use in context of the present invention include compositions wherein the proteins or oligonucleotides are contained in an amount effective to achieve the intended purpose. In one embodiment, determination of the effective amount is well within the capability of those skilled in the art.

Some examples of substances which can serve as carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the compound is basically determined by the way the compound is to be administered. If the subject compound is to be injected, in one embodiment, the pharmaceutically-acceptable carrier is sterile, physiological saline, with a blood-compatible suspending agent, the pH of which has been adjusted to about 7.4.

In addition, the compositions further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweeteners (e.g., aspartame, citric acid), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

The compositions also include incorporation of the proteins or oligonucleotides of the invention into or onto particulate preparations of polymeric compounds such as polylactic acid, polglycolic acid, hydrogels, etc., or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

In some embodiments, the proteins or oligonucleotides of the invention modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. In another embodiment, the modified proteins or oligonucleotides of the invention exhibit substantially longer half-lives in blood following intravenous injection than do the corresponding unmodified compounds. In one embodiment, modifications also increase the proteins or oligonucleotides solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound.

The following examples are presented to provide a more complete understanding of the invention. The specific techniques, conditions, materials, proportions and reported data set forth to illustrate the principles of the invention are exemplary and should not be construed as limiting the scope of the invention.

EXAMPLES

Experimental Procedures

Algal Growth Conditions

*P. incisa* was isolated and maintained (Watanabe S et al. *Parietochloris incisa* comb. nov. (Trebouxiophyceae, Chlorophyta). Phycol. Res. 1996, 44, 107-108) and subsequently axenic cultures of *P. incisa* were cultivated on BG-11 nutrient medium (Stanier R. et al. Purification and properties of unicellular blue-green algae (order Chroococcales). Microbiology and Molecular Biology Reviews 1971, 35, 171-205) in 250-ml Erlenmeyer glass flasks in an incubator shaker at a speed of 170 rpm, under an air/$CO_2$ atmosphere (99:1, v/v), controlled temperature (25° C.) and illumination (115 μmol quanta $m^{-2}$ $S^{-1}$) (Bigogno C et al. Biosynthesis of arachidonic acid in the oleaginous microalga *Parietochloris incisa* (*Chlorophyceae*): radiolabeling studies. Lipids 2002, 37, 209-216).

Construction of a *P. incisa* cDNA Library

One microgram of total RNA was reverse-transcribed into cDNA using a Verso™ cDNA kit (ABgene, Surrey, UK), according to the manufacturer's instructions. Each 20 μl reaction mix contained 1 μg of total RNA, 300 ng of random hexamers and 125 ng of anchored oligo-dT, dNTP mix (500 μM each), cDNA synthesis buffer, RT enhancer, and Verso enzyme mix. Following cDNA synthesis at 42° C. for 1 h, reactions were stopped by heating at 95° C. for 2 min and cDNA was diluted tenfold with PCR grade water.

Cloning of the PiAHAS cDNA

Several known amino acid and nucleotide sequences of the AHAS gene in related green algae and other higher plants were aligned, using ClustalW, retrieved from the Internet to identify conserved motifs in the enzyme. The conserved "blocks" were used to design two oligonucleotide primer sets, AHAS01 and AHAS02, for cloning partial PiAHAS sequences. All the primers used for PCR and sequencing are listed in Table 1. All the primers were designed by Primer3, version 0.4.0, retrieved from the Internet, software and checked with NetPrimer retrieved from the Internet. PCT amplifications were carried out using the first strand cDNA as a template, primers and 2xPCR ReddyMixTM Master Mix (ABgene), PCR amplification was as follows: denaturation at 94° C. for 3 min. followed by 32 cycles of 94° C. for 30 s, 60° C. for 90 s and 72° C. for 1 min, and a final extension cycle of 72° C. for 10 min. All amplified products were cloned into Pgem T-easy plasmid (Promega, WI, USA) and sequenced. The cloned fragments were analyzed by BLASTX.

The amplified fragments were used for the design of a third primer set, AHAS03. PCR amplifications were carried out using the first strand cDNA as a template, primers and 2xPCR ReddyMixTM Master Mix. Touch-Down PCR (TD-PCR) amplification was as follows: denaturation at 94° C. for 2 min, followed by 30 cycles of 94 ° C. for 30 s, 55° C. for 60 s and 68° C. for 1.5 min, and a final extension cycle of 68° C. for 10 min. The complete internal fragment was used for gene-specific primers (GSPs) design to clone the full-length cDNA of the PiAHAS gene, employing the 3' and 5' rapid amplification of the cDNA ends (RACE) method, using a BD smart RACE cDNA Amplification Kit (BD Biosciences, Clontech, Calif., USA) according to the manufacturer's manual. Two sets of RACE-cDNAs were synthesized for 3' end and 5' end amplification. The synthesized cDNA was used for PCR amplification of the 3' cDNA end using the Universal Primer A Mix (UPM) and the 3'AHAS GSP. The PCR amplification was carried out using the BD Advantage™ 2 PCR Kit (BD Biosciences). PCR amplification was as follows: denaturation at 94° C. for 2 min, followed by 30 cycles of 94° C. for 30 s, 63° C. for 30 s and 72° C. for 2 min, and a final extension cycle of 72° C. for 10 min; the reaction was terminated at 10° C. For the synthesis of the 5' cDNA end of AHAS, 5'AHAS GSP was used as a reverse primer and UPM as a forward primer and TD-PCR was employed: denaturation at 94° C. for 2 min, followed by 5 cycles of 94° C. for 30 s, 70° C. for 40 s and 72° C. for 2.5 min, followed by 5 cycles of 94° C. for 30s, 68° C. for 40s and 72° C. for 2.5 min, and finally 25 cycles of 94° C. for 30 s, 64° C. for 40s and 72° C. for 2.5 min.

An additional set of primers, PiAHAS-full, was designed based on the cDNA ends. The primers contained the start and stop codons and had SalI restriction sites for future ligations. PCR amplifications were carried out using the first strand cDNA as a template, primers and the PfuUltra DNA polymerase (Stratagene). PCR amplification was as follows: denaturation at 94° C. for 3 min, followed by 30 cycles of 94° C. for 30 s, 65° C. for 60 s and 72° C. for 3 min, and a final extension cycle of 72° C. for 10 min. The full gene was ligated and cloned into pGEM T-easy plasmid.

TABLE 1

Primers used in cDNA cloning

| Oligo | Sequence | Tm [C. °] | SEQ ID NO. |
|---|---|---|---|
| AHAS01-F | AACCGGCGCACACGTAC CTGG | 67 | 5 |
| AHAS01-R | CGGGGATCATGGGCAGCACG | 67 | 6 |
| AHAS02-F | GGCACCGAIGCITTICAIGAIAC | 68 | 7 |
| AHAS02-R | ACGGTGCCITGCATICCIAICAT | 69 | 8 |
| AHAS03-F | AGATCACCAAGCACAACTTCCT | 60 | 9 |
| AHAS03-R | ATGACAAAGTCG GGGAAGATGT | 60 | 10 |
| 3'AHAS GSP | ACGCTGGACGAGAGCCACATCT TC | 69 | 11 |
| 5'AHAS GSP | CCCTGTGATGGCAACAAGCGGA AC | 69 | 12 |
| PiAHAS-full F | ATA*GTCGAC*AGCATGCAAGGCA CTATG | 68 | 13 |
| PiAHAS-full R | AAT*GTCGAC*CTGCGCCTTAGTA CTCG | 69 | 14 |
| AHAS-Mut-F | GCATGGTGGTCCAGT**c**GGAGGA CCGCTTCTACA | 79 | 15 |
| AHAS-Mut-R | TGTAGAAGCGGTCCTCC**g**ACTG GACCACCATGC | 79 | 16 |
| pAH29-empty-F | TATA*GTCGAC*GCGCAAAAGGAA TATAAAAA | 65 | 17 |
| pAH29-empty-R | TATA*GGATCC*CATAGTTAGTTCC CCGTCC | 70 | 18 |
| PiAHAS-ORF | *GGATCC*ATGCAAGGCACTATG | 63 | 19 |
| PiAHAS-trunc | *GGATCC*AATGAGCTGGTGGC | 61 | 20 |
| PiAHAS-R | *GTCGAC*CTGCGCCTTAGTACTC | 66 | 21 |

Site-directed Mutagenesis of the PiAHAS Gene

A specific point mutation was designed for substitution of the PiAHAS Trp605 with Serine. Mutagenesis of the PiAHAS wild type cDNA was performed with the QuikChange site-directed mutagenesis kit (Stratagene, Calif., USA). A complementary oligonucleotide primer set, AHAS-Mut, was designed with the intended point mutation. PCR amplification was carried out using the pGEM T-easy plasmid with the AHAS gene as a template, primers and the proofreading PfuUltra DNA polymerase (Stratagene). PCR amplification was as follows: denaturation at 94° C. for 1 min, followed by 12 cycles of 94° C. for 30 s, 55° C. for 60 s and 72° C. for 5 min, and a final extension cycle of 72° C. for 10 min. After the PCR reaction, the parental DNA template was digested with DpnI restriction enzyme. The PCR amplified plasmid was separated on agarose gel, extracted and inserted into *E. coli* competent cells. Ampicillin resistant colonies were selected from which the plasmid was extracted. The extracted plasmid was sequenced for confirmation of the desired point mutation.

PiAHAS Functional Expression in Bacteria

*E. coli* K12 strain BUM1 is a recA mutant of strain CU9090 which does not express any AHAS enzymes and cannot grow on minimal medium lacking isoleucine or valine (Ibdah M, et al. Homology modeling of the structure of bacterial acetohydroxy acid synthase and examination of the active site by site-directed mutagenesis. Biochemistry (N.Y.) 1996, 35, 16282-16291). This strain also requires proline and thiamin, regardless of AHAS expression. Transformation of BUM1 cells was achieved using a standard heat shock protocol. BUM1 cells were grown in LB or in M9 minimal medium (7 mg/ml Na2HPO4; 3 mg/ml KH2PO4; 0.5 mg/ml NaCl; 1 mg/ml NH4Cl; 0.12 mg/ml MgSO4; 0.35 mg/ml thiamin HCl; 2 mg/ml glucose) supplemented with 200 μg/ml proline. Where appropriate, the M9 medium was supplemented with the BCAAs valine, leucine, and isoleucine (150 μg/ml of each) or with 50 μM SMM. BUM1 transformants were propagated and kept on LB medium supplemented with 100 μg/ml Ampicillin. For functional expression assays, the cells were washed and plated on M9 agar plates and incubated for 48 hrs at 37° C.

The expression vector pAH29 (Lawther R et al. Molecular basis of valine resistance in *Escherichia coli* K-12. Proc. Natl. Acad. Sci. U. S. A. 1981, 78, 922-925) contains the ilvGM genes (i.e., the entire coding region of *E. coli* AHASII large and small subunits) under the native bacterial promoter of the ilvGMEDA operon, ilvEp (Lopes J et al. Analysis and comparison of the internal promoter, pE, of the ilvGMEDA operons from *Escherichia coli* K-12 and *Salmonella typhimurium*. Nucleic Acids Res. 1986, 14, 2779-2798). The pAH29 plasmid was used as a template for amplification of the plasmid back-bone with pAH29-empty primer set, without the ilvGM coding region. To clone the PiAHAS cDNA, three primers were designed. PiAHAS wild type and mutant genes were amplified with the forward primers, PiAHAS-ORF and PiAHAS-trunc, designed to include and exclude the estimated 90 amino-acids chloroplast targeting peptide, respectively. The forward primers were also designed to include BamHI restriction site. The reverse primer PiAHAS-R included a SalI restriction site and was designed based on the 3' end of the gene.

PiAHAS in vitro Enzyme Assay

To overexpress the hexahistidine (6xHis)-tagged PiAHAS genes in *E. coli* strain JM109, plasmids pQE-WT and pQE-MUT were used. These plasmids were constructed by inserting the BamHI-SalI fragment containing the cloned PiAHAS wt and mutant genes into plasmid pQE30 (Qiagen, Hilden, Germany). These plasmids express PiAHAS fused at its N-terminus to the pQE30 6xHis leader. pQE-WT and pQE-MUT were transformed into *E. coli* for expression. The transformed cells were grown, IPTG induced, and harvested as described previously (Hill C et al. Purification of *Escherichia coli* acetohydroxyacid synthase isoenzyme II and reconstitution of active enzyme from its individual pure subunits. Biochem. J. 1997, 327, 891-898). Bacterial cells were disrupted by sonication in a binding buffer with 20 mM imidazol, 0.5 M sodium chloride, 50 mM sodium dihydrogen phosphate (pH 8.0), 20 μM FAD and 50 μl/g cells of protease inhibitor cocktail (Sigma-Aldrich, Israel). After 30 min of centrifugation at 20,000×g, the supernatant was loaded on a 1.5×8 cm column of Ni2+-nitrilotriacetatic acid-agarose (Qiagen) previously washed with the binding buffer. The column was then washed with 80 ml of the binding buffer, and the His-AHAS protein eluted with 0.4 M imidazol in the binding buffer. The fractions were dialyzed against 50 mM potassium phosphate buffer (pH 7.6), containing 20 μM FAD. The protein was concentrated for storage at −20oC by dialysis against same buffer, containing 50% glycerol. The AHAS catalytic activity was determined as previously described (Bar-Ilan A et al. Binding and activation of thiamin diphosphate in acetohydroxyacid synthase. Biochemistry (N.Y.) 2001, 40, 11946-11954). The reactions were carried for 20 min at 37oC in 0.1 M potassium phosphate buffer (pH 7.6), containing 10 mM magnesium chloride, 0.1 mM ThDP, 75 μM FAD, 5 mM EDTA, 1 mM DTT with 100 mM pyruvate as substrate, except where otherwise indicated. The activity is expressed in units (U) (1 U=1 μmol of acetolactate formed $min^{-1}$). Km for pyruvate and Ki for SMM were determined by varying the concentration of the factor in question. Protein concentration was determined by the dye-binding method of Bradford (Bradford MM. A rapid and sensitive method for the quantitation of microgram quantities of protein utilizing the principle of protein-dye binding. Anal. Biochem. 1976, 72, 248-254), with bovine serum albumin as standard. Km calculations were fit with the program "Sigma-Plot" to Michaelis-Menten equation. For Ki calculations, the lines were fit to equations:

$$V=Vo\times Ki/(Ki+[SMM]), \text{ for wild-type;}$$

$$V=Vf+(Vo-Vf)\times Ki/(Ki+[SMM]), \text{ for mutant.}$$

V is the rate of acetolactate formation by AHAS;

Vo and Vf are beginning and final rates of acetolactate formation;

[SMM] is concentration of SMM;

Example 1

Cloning of PiAHAS cDNA of *P. Incisa*

Multiple sequence alignment, by ClustalW, of the AHAS protein sequences of the green algae *Chlorella variabilis* (EFN51096.1), *Chlamydomonas reinhardtii* (AAB88292.1), and *Volvox carteri* (AAC04854.1), the moss *Physcomitrella patens* subsp. (XP_001759950.1) and the higher plant *Brassica napus* (AAA62705.1) showed 4 conserved sequence blocks, designated A-D (FIG. 1). The first set of primers, AHAS01, amplified a 250 by region of the C-terminal part of the gene between Block C and Block D. The second set of primers, AHAS02, was of a degenerate nature in which inosine was introduced at positions of non-conserved nucleotides, amplified a 500 by region of the N-terminal part of the gene between Block A and Block B. The amplified products were found to contain partial AHAS coding sequences. Based on these cloned sequences we designed a third primer pair, AHAS03, which was used to amplify a single band of about 1200 by in size, extending from Block A to Block D. This complete 1200 by fragment was cloned and sequenced and found to encode the PiAHAS gene. The 5' and 3'-ends of the PiAHAS cDNA were amplified from the RACE Ready cDNA. RACE-PCR enabled amplification and cloning of the gene ends, including 800 by of the 3' untranslated region (UTR) and 80 by of the 5' UTR. The clones were sequenced and PiAHAS-full primer set was designed and used to amplify the complete 2100 by AHAS coding sequence.

Example 2

Prediction of PiAHAS Chloroplast-Targeting Signal

The putative PiAHAS protein was found to be 70-75% identical to the AHAS proteins of the green algae *C. variabilis, C. reinhardtii*, and of *V. carteri*. When these proteins were aligned by ClustalW (FIG. 2), we found low conservation in the N-terminus between these different green algae. The first ~100 amino-acids of the PiAHAS N-terminus showed poor similarity to the other proteins, particularly by the presence of a unique polyQ repeat. We analyzed the encoded protein for the presence of possible chloroplast transit peptides using ChloroP and TargetP softwares. Neither predicts plastidial localization for PiAHS.

Example 3

PiAHAS Site-Directed Mutagenesis pGEM-T Easy vector, harboring PiAHAS cDNA, was used as a template for site-directed mutagenesis by PCR amplification with AHAS-Mut primers, carrying the desired W605S mutation. The reaction resulted in pGEM-T Easy, containing the mutagenized PiAHAS insert (PimAHAS). The mutation was verified by DNA sequencing.

Example 4

Growth Complementation of AHAS-Deficient *E. coli* by PiAHAS and PimAHAS

The expression vector pEp-empty, an empty plasmid that retains the native ilvEp promoter and ATG start codon, was created by amplification of pAH29 plasmid with the pAH29-empty primer set, and included BamHI and SalI restriction sites for future fusion with the algal genes. Three forms of PiAHAS genes were used for this experiment: PiAHAS full open reading frame (ORF), truncated PiAHAS without the estimated chloroplast targeting peptide (from Serine91), and PimAHAS containing the point mutation (W605S). The three forms were amplified and digested with BamHI and SalI. Each PiAHAS form was inserted into the pEp-empty, under the native bacterial promoter to form three constructs: pEp-ORF, pEp-truncated and pEp-mut. A vector containing only the Ep, pEp-empty, was used as a negative control. The four constructs, together with pAH29 as a positive control, were transformed into E. coli BUM1 competent cells. The transformed cell lines were plated on three types of agar plates: M9, M9 supplemented with BCAAs and M9 supplemented with 50 μM SMM. The plates were incubated for 48 hrs (FIG. 3) and bacterial growth was determined. All the cell lines were able to grow on the BCAAs supplemented medium. The M9 plates, without BCAAs, were used to select for bacteria with functional AHAS activity. The host strain, BUM1, transformed with the pEp-empty vector was unable to grow on these plates. In contrast, bacteria transformed with the different PiAHAS genes were able to grow on the selective medium, as were cells transformed with pAH29. This result indicates that the algal PiAHAS gene can functionally complement the bacterial mutation, and that the first 90 amino-acids are not required for enzymatic activity. To test whether PimAHAS conferred SMM resistance, we added 50 μAM SMM to the M9 plates. Growth was totally inhibited in the bacteria transformed with the wild type PiAHAS genes, whereas those carrying the mutant gene were not affected by the herbicide. Bacteria transformed with pAH29 were able to grow slowly in the presence of 50 μM SMM, probably due to higher level of SMM resistance of the bacterial AHASII enzyme (Steinmetz, A et al. Valine 375 and Phenylalanine 109 Confer Affinity and Specificity for Pyruvate as Donor Substrate in Acetohydroxy Acid Synthase Isozyme II from *Escherichia coli*. Biochemistry (N.Y.) 2010, 49, 5188-5199).

Example 5

Biochemical Assay of PiAHAS Activity in Vitro

Figure 4:
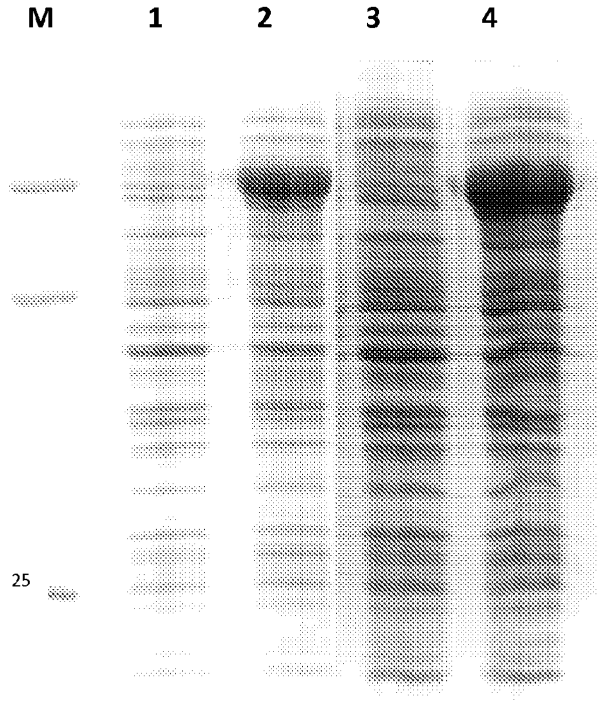
FIG. 4. Is a micrograph of a SDS-PAGE analysis of IPTG induction of wild-type and mutant PiAHAS. Protein marker (M), Lane 1: wild-type PiAHAS before induction, lane 2: wild-type after induction, lane 3: mutant PiAHAS before induction, and lane 4: mutant PiAHAS after induction. 75 kD recombinant protein over-expression is visible.

*P. incisa* genes encoding the wild-type and mutant forms of AHAS were cloned into the pQE30 expression plasmid and expressed in *E. coli* JM109 cells as N-terminal hexahistidine-tagged proteins. The molecular weights of the AHAS forms are shown on a Coomassie-stained sodium dodecyl sulfate-polyacrylamide gel electrophoresis (SDS-PAGE) gel (FIG. 4). Total protein samples of the transformed bacteria, before and after induction, showed enhancement of a band of about 75 kDa, the expected size of the large subunit of the putative PiAHAS. The proteins were expressed in soluble form and were purified using Ni+-chelating column chromatography. Enzymatic parameters for interaction of the enzyme with its substrate and with the herbicide inhibitor were determined and presented in Table 2.

TABLE 2

Kinetic parameters for wild-type and mutant AHAS[a].

| Parameter | Wild-type | Mutant |
|---|---|---|
| Specific activity, U × $mg^{-1}$ | 3.00 ± 0.05 | 1.46 ± 0.03 |
| $K_m$ for pyruvate, mM | 49.4 ± 2.1 | 71.7 ± 2.9 |
| $k_{cat}/K_m$, $M^{-1} \times s^{-1}$ | 83 | 25 |
| $K_i$ for SMM, μM[b] | 0.15 ± 0.01 | >30 × $10^6$ |

[a]The kinetic parameters were determined as described under Materials and Methods at 37° C. and pH 7.6.
[b]The concentration of pyruvate was 100 mM.

Figure 5:
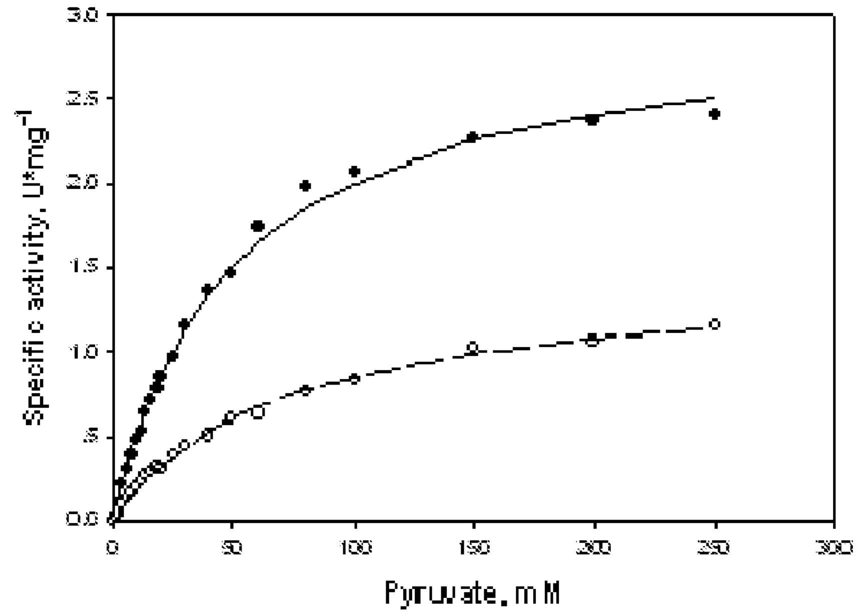
FIG. 5. Is a graph showing pyruvate dependence for PiAHAS wild-type and its mutant. The reactions for AHAS wild-type (●) and its mutant (○).

Enzymatic activity of the wild type and mutant forms of AHAS in the presence of different Pyruvate substrate concentrations was assayed with 6.9 μg/ml of PiAHAS wild-type protein and 11.5 μg/ml of mutant protein (FIG. 5) and the specific activity and Km were calculated. The specific activity of the purified PiAHAS was 3 U/mg, whereas the tested mutant W605S showed a 2-fold decrease.

Figure 6:
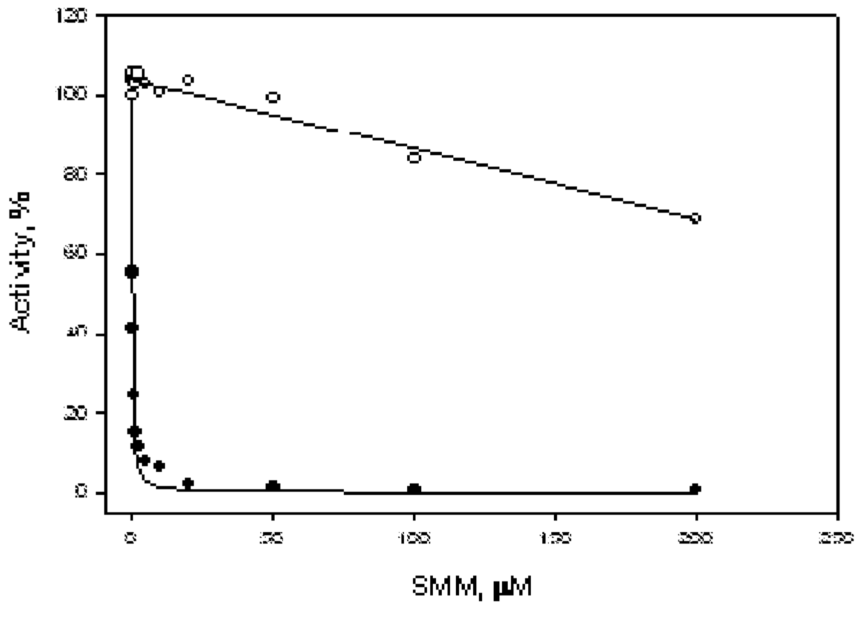
FIG. 6. Is a graph showing inhibition by SMM of AHAS wild-type (●) and its mutant (603 ).

The inhibition of the *P. incisa* wild type and mutant enzymes, by different SMM concentrations, was also assayed with 8.3 μg/ml of PiAHAS wild-type protein and 23 μg/ml of mutant protein (FIG. 6). The wild type form was strongly inhibited by very low concentration of SMM and its Ki was determined to be 0.15 μM. W605S substitution on the other hand, showed strong resistance to this herbicide, even at high concentrations of 200 μM. The Ki was determined to be >30×106, 7 orders of magnitude higher than that of the wild type.

In summary, the gene encoding PiAHAS was successfully isolated and cloned. The gene was further mutated at a Trp residue. The wild type and mutant genes were functionally expressed in AHAS-deficient bacteria. The genes were shown to complement AHAS activity in vivo and the mutant form was shown to confer SMM resistance. In green algae and higher plants AHAS is encoded in the nucleus and typically, the protein is targeted to the chloroplast by N-terminal chloroplast-targeting signal. Commonly used softwares, like ChloroP and TargetP, did not identify the protein as plastidial targeted, suggesting a unique, species-specific, chloroplast targeting peptide sequence. It was shown that a truncated protein, lacking the first 90 amino-acids of the N-terminus, retained its enzymatic activity in-vivo (FIG. 3). The wild type and mutant proteins were cloned into pQE30 vector, expressed as his-tagged proteins, isolated and characterized in-vitro. The molecular weight of the protein was determined to be 75 kDa by SDS-PAGE (FIG. 4). The W605S mutation caused a 2-fold decrease in enzymatic activity and in the affinity to the Pyruvate substrate, compared to that of the wild type. The mutant protein showed 7 orders of magnitude higher resistance to the SMM herbicide than that of the wild type.

Example 6

Herbicide Sulfometuron Methyl (SMM) Resistance to the Endogenous Copy of AHAS Gene Combination of native regulatory elements and natural codon-usage was shown to drive efficient and stable expression of the endogenous marker-gene in algal cells as compared with antibiotics resistant genes. To facilitate stable nuclear transformation of *P. incisa* cells, in this experiment the same mutation, responsible for resistance to herbicide sulfometuron methyl (SMM), was introduced into the endogenous copy of AHAS gene: gDNA sequence of the gene was retrieved by blasting of cDNA to *P. incisa* genome sequence (giavap-genomes.ibpc.fr).

Figure 8:
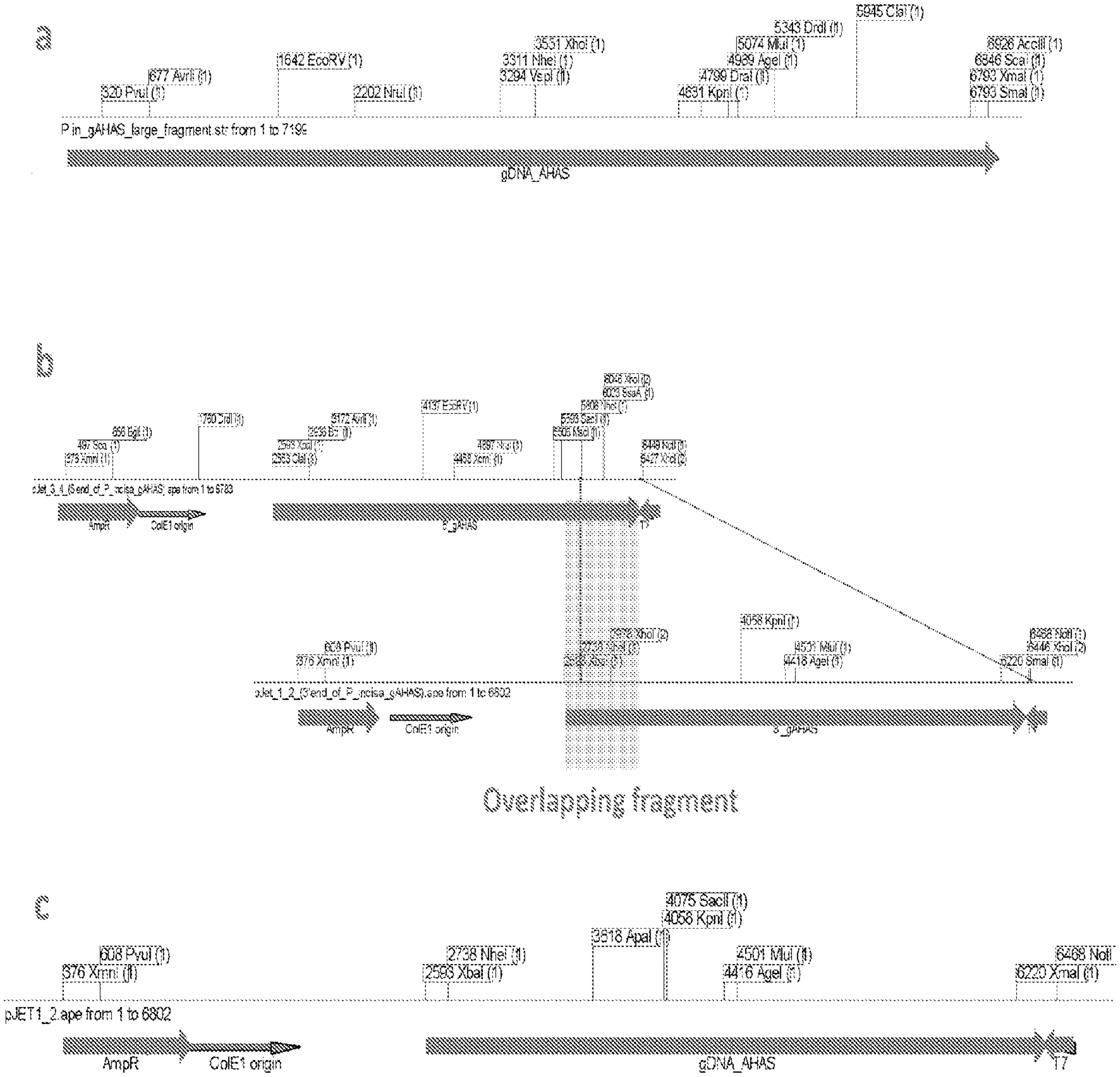
FIG. 8. Is a scheme showing *P. incisa* gAHAS cloning in to pJET 2.1 for achieving stable nuclear transformation. The structure of *P. incisa* AHAS genomic loci is provided in 8A; the structure of the two fragments of AHAS gene, cloned into pJet 2.1 vector with overlapping regions, the insertion of 3' AHAS fragment by Nhe I, Not I restriction sites are provided in 8B; the structure of the assembled genomic fragment of the *P. incisa* AHAS gene, cloned into pJet 2.1 vector is provided in 8C.

For amplification of an AHAS gene, utilizing its endogenous regulatory elements, 5' forward primer in 1 kb upstream to ATG translation initiation codon and 3' primer in 0.15 kb downstream after TAA translation Stop-codon, were used. Due to the large size of the whole amplicon, (7.2 kb), internal primers for amplification of two overlapping fragments of AHAS genomic loci were designed. After amplification, fragments with 5' and 3' parts of AHAS gene were cloned into pJET 2.1 (Fermentas) cloning vector. Then, 3' fragment was mutagenized according to adapted Quick-Change (Stratagene) protocol and the whole chromosomal fragment was assembled by insertion of NheI-NotI fragment of 3' part of AHAS gene into NheI-NotI restriction gate in plasmid with 5' of AHAS gene (FIG. 8. *P. incisa* gAHAS cloning). For amplification of 5' and 3' parts of AHAS genomic loci following pair of primers were used: AGAGGGGCATCAAAACCAGG (SEQ ID NO: 22) CGTAGTTGGCGTACACCGTA (SEQ ID NO: 23) and CCTCAGCGACGATCCTCTTC (SEQ ID NO: 24) CCATACCAGGCCCATTGTGT (SEQ ID NO: 25). Point mutation was introduced with primers ctgggcatggtggtccagtCggaggaccgcttctacaag (SEQ ID NO: 26) and cttgtagaagcggtcctccGactggaccaccatgcccag (SEQ ID NO: 27).

The actual sequence encoding the genomic fragment of *P. incisa*, containing AHAS gene is:

(SEQ ID NO: 28)

```
AGAGGGGCATCAAAACCAGGgaaacagcctcgcgcaaaccagcaacaattgtgagcagcg

ctgtttgcggctgtgtgagtgctcggtcgctctgtggggcaggtgcttccactatcacattatcatgagattgccctgccatccc

tgctcctctctgccacgctgggcgagaaggagctgtcgaaatcgcctccaggagtggccgtgactgcgatcgagttgacgt
```

-continued tagcacctgaatagtggtactggcacttcagagatagctgcaggtcagcatgcaaggcaccatgcggccgacggctggag cactgcagcagaccgtcggctgctggcacgtcccggccggcatcccccacgcacagcaggtgtttcaagttgttaggtggt gataagtgcctactgaagattcctttatgcagctgaacgaggcagcgtcccttgcttcccagatcaacagccccttgtcactgg tctgacaaaacgtgtgtgacaccctgacctgcgcatgcaggcgctgcgaggccgtatactgcccgaggagctgaagcagc ggtgttcagcaaccaaacctaggtacaattgcagcagtagctcgacatgcatacacgcttaacgcagctgctggcagcagtc tcgtgcctactgcttgccgccgcagcatgggctggctaccactacccttgaaacacacacaaggctcacaaaggtcctccct ttcgtcccttgaggcagatgtgacgcctgctttgaccctgtgcacagggcggccaggcagtcagcggtgaccgctgccaag cttgcagagggcaaggcaggcacaccatcacggagcttgcggcagcagccggcagcgccgcagcagcagcagcagca gcannnnnnnnnnnnnnnnnnnnnnnnnnnnnnnnnnaggtcgtctggcacgggtggcaggtggcacgctcttcag gcacttggtttggacaccctagcagtatgtcgtcgagttcagATGGAAGTCCTAGTACAGTGTGAGgt cagcgttggcaagcctgccttgtcaatgtggcacactgatgcctttgcgcagcacatgcggatggggtggagtgtcgcatga gctggcatggtccagttggaccctgctggggatgctgctagtatgggttgctggaccagatgaccctggtcttgagtggtga ccatggcgccagtgcatccaactgctggtgtggtttgcttctgccccagctgtcaagctactgcaggccgggcggtgcagg caaaacaccaggcagtacatgtagcagcttgacggcagttgtagtagctcaccgccaccaatagtttgacgcactggcaga ctacctcagggcatgcctgcagctgctgtggcaagagggcatgagcctatccaatgcagctgctgtgaccacacatacctg gcctgtctgtgcagCTGGTGGCGTTGCGGGAGGCTGCCAAGGCCTCGCTCTCATCC

CCCGCGCCAGCCGAGTGGGTGGATCGGTTTGGGTCGGAGCCCCGCAAGGG

CGCGGATATCCTGGTGCAGTGCCTGGAGCGCGAGGGGGCCTTCCGCGTGTT

TGCCTACCCCGGCGGCGCCAGCATGGAGATCCATCAGGCCTTGACGCGCA

GCGGCATCATCCGCAACATCCTGTGCCGCCATGAGCAGgtggggatggaccagactg gcctggtgtggggcgaacaagtaggaaccagtgggccacggcacaggcggtacacatgcgtatggcatgggaggctgat agtgctcgcatgtagggatggcattttgcctgccaaagggcttggctatgcttgtgatgcacagtgggcctgcatctgagcac tgaagccagtcagtcattggctgattgatgaatgccgcttcacccagtgacagatgcattggcctcgggtgtggttcaaagct acagcaactgaaggacgctgagggcatgtgcatgtccaccaccttcacttactgtcaagtcttgcctacccatgcctgatcca gcatgaacgccatgtcgcagGGCGAGATCTTTGCGGCGGAGGGCTATGCCAAGTGCAC

GGGCGATGTGGGCGTGTGCATCGCGACCAGCGGGCCCGGCGCCACCAACC

TCGTGACTGGCCTGGCTGATGCCATGCTGGACAGCGTTCCGCTTGTTGCCA

TCACAGGGCAGgtgtgcacgcaagtcatcctgttgtttctcggcctgcctgtatggtctgtagcctgtttcaggtgct ctgctcagcatcgcagatgcctcactgctttctgttgtggcgggggtcactaacctgcataaagtttccaccttgagcagtcgtt caagcactactacttgtactgacagtcaacaatgagtccactgatcaggctacgaatgcaatgtggcggctgctcgaccacat gtcagcgctctggcagtaaaccggggttccgcatgcaggTGCCCCGCAAGATGATCGGCACGGAC

GGGTTCCAGGAGACGCCGATTGTGGAGGTGACGCGGCAGATCACCAAGCA

CAACTTCCTGGTCATGGACCTGGATGACCTGCCGCGCATCATGAAGGAGGt aggtgtggttcacctgcaacagaagcaaggcaatgtgcttgcacagcctgctcttctgcgcacagcagtccctgctgattgct tgtttggaagctaggcaacagctgctgcagacgcacaagcaacatcacatgcagaggcatcacacgcgattttggcaacct gccggctaggtggcctaatcctgactctctatcaccctgtctgtttttgcaggCATTCTACCTGGCGCGCAC

GGGGCGGCCGGGCCCGGTGCTGGTGGATGTGCCCAAGGACATCCAGCAGC

AGCTGGCGGtgccggactgggacacgcccatggccatcagcggctacatgtcgcgcctgccnnnnnnnnnnn nnnnnnnnnnnnnnnnnnnnnncccgcctaacccctcacagctggccgcggtcgtgcgcgcgctgaaggaggtacg catgggtgatgcgcagcctcggtcgcctttctgaagtagacagcacgacctcagcgacgatcctcttcagttgagccgtgcc -continued catgcatgcatgtaagtgcatggatgcaagcatgctgaatcgctttctgagacagactgtgcatgctatgggcaaggtacatc attaatggaaagttgctgctagctgcaagcctgcgaaccggccccgctttcaccagcgtttggtcgccttcagcacagtgcac ctgtccatacggaacgcttctttcccacatcatgcacggtgcatcatgcacggtacaatcaagctgtctggcgtgataaggag ccgtggctgacatctcggcaggaaacttatgctttccccacttcctgtaggCTAAGAGGCCGACGCTGTAC

GTGGGCGGTGGCGCGCTCGACTCGAGCGCTGAGCTGCGCGAGTTTGTGCG

GCTGACGGGCATCCCCGTCGCGCAGACGCTTATGGGCCTGGGCACCTTCCC

CGAGGAAGACCCGCTGGCACTGCAGgtaggcttccttgctggcgggagactggtaacaaaggagg gagcagtttgtgagcctatgggtgcgggacagtgcgagatctggttgaatgatgtgttgtcatgcggcttgtgacacgttgtg gcacctgcggcagctggatgccatcttatgggcagccatggcaccagcgcgtggggctatgggtcatgctgacaaggcca gtgccattgttttggatgcagATGCTGGGCATGCACGGTACGGTGTACGCCAACTACGC

CGTCAACGACAGCGACCTGCTGCTGGCGTTTGGCGTGCGCTTCGACGACCG

CGTGACTGGCAAGCTGGAGGCGTTTGCTTCGCGCGCGCATCGTGCACAT

CGACATCGACCCTGCGGAGATCTGCAAGAACAAGGAGGCCCACATACCCA

TCTGTGCAGgttggttcgtatagagcagcacccattttgttttcgatgtcagtgcaaatgctagaaagccagttttgaca gccagcacctcatgcagggctatgtatacttgcatactcagggcccgactgggcatgttgactgccaggttccttactgctcat gttggctgcagACCTGCGTGCGTCGTTGATAGCGCTGAATGAGCTGTTGCGGCGA

GACCCTCTGCCAGAGGGCGCCTTTGCGGACTGGCGGGCGGCCATTGAGGC

CAAGAAGCAGGAGTTCCCCATGACCTTCCCGGAGCGGGACGACGTGATCA

TCCCACAGCGTGCCATCCAGGTGAGAGGCGATGTCATGGATTCAgtgagacagc cgcaagacatgttggcatgacatgttttcctctctgttctcttgctgggaatgtcattgtttgcgagcaggccacatctgcaagca aaaccgtcttgcttgcctcgtgcagATGCTGTATGAGGAGACAAACGGCGAGGCCATCAT

CAGCACCGGCGTGGGCCAGCACCAGATGTGGGCGGCGCAGTGGTACCAGT

ACAACGAGCCGCGGAGATGGGTCACGTCCGGCGGCCTCGGCTCCATGGGC

TTTGGCCTGCCATCCGCCCTCGGCGCGGCGGTGGCCTACGACGGCACGGAC

GGTCGGCCCAAGAAGGTatccgtcatatggaatcctctggctgaatggcatgcctttttttaaactctgcctggt atctgggtgaaagcgggtgaaagcgatgtctggccctacaaggagttggcgtgccactagaaatgcctgtgatagcaccaa tctctgtttggagagagttcattgttgtatgaaggatacggggcaacccttgatccatgtacatacatgtctgtatgtgccctcgc tgtttgaccggtcaggtgagcgtgcatggtgctgcactgggctacccagtgcagagggatgtaggctgccatctgtgttcgtc tagccgtgacgcgttttgtcaatgtatcatcagctggcgggtatggcaaccaaagatggtaagcttggatgatgagggtgacc tgttacctgacccagcgctctggcaaggcccttcatcatccagcgttactctactggctacattggttcagtggcggacggtgt atctgctaggttgtgcacaccagtcagccagatgctggtagggcaattggttgtcctcctatgagccaacgacgacctttgct gatcgggtgtcaccctgacgcaggcttgaccatgaagtctaagtagacgatgctgcttttcgcacacctctgctcaataaaata tgtggttggcatatgtgcatggccaagtgtgcggcatgaccagctgtctataaggccccgacatagctggcctttgttaggct gacgcctcatgaggttgctgccatcatcttgaccgctcacatggtatgacgacggttatgacgacggttatgacgacggttat ggcacgtggttgagcgtggtcaggtcctcgcatcacactacaatctttacatgcagatgctgtgtgcctatttgtgtgttatgga gatagcatcgacggcaggccagcagcctacaaggcagcggggactaaagcagtggatctggtgaccttgcttcgtagttg ccactaccaggcaatagcaacatggggatcttgcagttgcaaggctcagcttgtgactcaatctcgggcattgcgtccaatct tgtgcaggcgaggtggacgtggacatctaagtgtatgcttgctgacctgctaaaagtgtctgagtagaagcagtgaatatccg acgtggcatcaaggagtgagccgccttgtcgcgcaggtcgtcgtggacatcgatgatggccacagcttctgaagattcgca cacagcatcctgttggaacatgaggcttgcctgcgcaggtGGTGGTGGACATCGACGGCGACGGC

AGTTTCCTGATGAACTGCCAGGAGCTGGCGACGGCGGCGGTGGAGGGCCT

-continued

GGAGACCAAGATCATGATCCTCAACAACCAGCACCTGGGCATGGTGGTCC

AGTGGGAGGACCGCTTCTACAAGGCCAACCGCGCACACACCTACCTCGGC

CACCGGGtgcgtcccacaggctgctggtcttgccggtttcggtccagctgacttgttgtgacgctgttattgctggtgct gtgtgagactgacatgaagttgctcttgcaagaggttggggcagagtggcagtgaaaaataagttgcaggcttcaaaccac gcaatgcatgcaggCCAATGAGTACCACACGACGCTGGACGAGAGCCACATCTTC

CCCGACTTTGTCATGATGGCCAAGTCGTGCGGCGTCCCAGGCCGGCGCGTC

ATCAAGCCCGAGGAGCTGCGCGGGGCCATCaggtgggggctgctgccacgggcgcagtgctt gcagcatgcacactgtctgcaacttggtgaaccctggctgtggtgtgtggagatggcacattaagcacgtgcatcgcactgc tgctgccaccctacaggtggagtccctctgctcttgctgcgctcgtcgcactggtggaagctcagcagctctattcctgcagc agctgctgaagtgatgtgtctccactgacaGGGAGATGCTGGACACGCCCGGCCCCTTCCTG

CTGGACGTGATGGTGCCGCATGTGGAGCACGTGCTGCCCATGATCCCGGGC

GGCGGCTCCTTCAAGGACATCATCACCAAGGGCGACGGCCGCGACGAGTA

CTAAggcgcaggtcgcataggttgccatgggcaaggggctgccatggttgacttggtcgtgaccgatggttgtctgtcc ggacgttttcggtaacgtcctgcgctgtcctgctaccaaggtgctgtgctgtaggcACACAATGGGCCTGGT

ATGG.

Detailed analysis and description of SEQ ID NO: 28 is further provided in FIG. 7.

---

The invention claimed is:

1. An expression vector comprising a polynucleotide, said polynucleotide comprises: (a) a nucleic acid sequence encoding a protein, said protein comprises the amino acid sequence set forth in SEQ ID NO: 1; or (b) the nucleic acid sequence of SEQ ID NO: 28.

2. A transgenic alga, a transgenic plant, or a transgenic seed, comprising the expression vector of claim 1.

3. The transgenic plant of claim 2, wherein said transgenic plant is a transgenic embryo or a transgenic shoot.

4. A cell transformed by the expression vector of claim 1.

5. The cell of claim 4, wherein the cell is derived from a transgenic alga, a transgenic plant, or a transgenic seed.

6. The cell of claim 5, wherein said transgenic plant is a transgenic embryo or a transgenic shoot.

7. A method for enhancing the production of branched-chain amino acid (BCAA) in a cell comprising the step of transforming a cell with the expression vector of claim 1, thereby increasing the production of BCAA in a cell.

8. The method of claim 7, wherein the cell is an alga cell.

9. The method of claim 7, further comprising the step of transforming said cell with a polynucleotide encoding an enzyme selected from the group consisting of: Threonine deaminase (TD), ketol-acid Reductoisomerase (KARI), dihydroxyacid dehydratase (DHAD); transaminase (TA), 2-isopropylmalate synthase (2-IPMS), 3-isopropylmalate dehydratase (3-IPMD) and 3-isopropylmalate dehydrogenase (3-IPMDH), or a combination thereof.

* * * * *